(12) United States Patent
Saxena

(10) Patent No.: US 11,904,060 B2
(45) Date of Patent: Feb. 20, 2024

(54) SYSTEM AND METHOD FOR CONTROLLING A UVC BASED AIRCRAFT SANITIZATION SYSTEM

(71) Applicant: HONEYWELL INTERNATIONAL INC., Morris Plains, NJ (US)

(72) Inventor: Sunit Kumar Saxena, Bangalore (IN)

(73) Assignee: HONEYWELL INTERNATIONAL INC., Charlotte, NC (US)

( * ) Notice: Subject to any disclaimer, the term of this patent is extended or adjusted under 35 U.S.C. 154(b) by 535 days.

(21) Appl. No.: 17/015,747

(22) Filed: Sep. 9, 2020

(65) Prior Publication Data
US 2022/0031878 A1 Feb. 3, 2022

(30) Foreign Application Priority Data
Jul. 28, 2020 (IN) .............................. 202011032291

(51) Int. Cl.
*A61L 2/10* (2006.01)
*A61L 2/24* (2006.01)
*B64F 5/30* (2017.01)
*A61L 2/26* (2006.01)

(52) U.S. Cl.
CPC ........ *A61L 2/10* (2013.01); *A61L 2/24* (2013.01); *A61L 2/26* (2013.01); *B64F 5/30* (2017.01); *A61L 2202/11* (2013.01); *A61L 2202/14* (2013.01); *A61L 2202/16* (2013.01); *A61L 2202/25* (2013.01)

(58) Field of Classification Search
CPC ........................................................ A61L 2/10
See application file for complete search history.

(56) References Cited

U.S. PATENT DOCUMENTS

| 8,226,887 | B2 | 7/2012 | Harmon et al. |
| 8,330,121 | B2 | 12/2012 | Douglas |
| 8,907,304 | B2 | 12/2014 | Kreitenberg |
| 9,364,573 | B2 | 6/2016 | Deshays et al. |
| 10,010,634 | B2 | 7/2018 | Bonutti et al. |

(Continued)

OTHER PUBLICATIONS

Control Systems—Introduction, Jan. 18, 2017, TutorialsPoint (Year: 2017).*

(Continued)

*Primary Examiner* — Kevin Joyner
(74) *Attorney, Agent, or Firm* — Lorenz & Kopf LLP

(57) ABSTRACT

A control system in a UVC-based aircraft sanitization system for controlling the UVC-based aircraft sanitization system to maintain a desired UVC (ultraviolet C) radiation level at a target surface in an aircraft under varying operating conditions is disclosed. The control system includes a controller configured to: receive measured radiation feedback from a radiation measurement device (e.g., dosimeter) on the target surface that identifies a radiation level that is applied at the target surface by the UVC-based aircraft sanitization system; and generate a UVC source control command for UVC sources in the UVC-based aircraft sanitization system, based on the received measured radiation feedback, to control the UVC sources to increase or decrease radiation level output (e.g., identify the amount of increase or decrease from the UVC sources) to generate sufficient radiation to achieve the desired radiation level at the target surface.

20 Claims, 10 Drawing Sheets

(56) References Cited

U.S. PATENT DOCUMENTS

| | | |
|---|---|---|
| 10,603,394 B2 | 3/2020 | Farren et al. |
| 2007/0023710 A1 | 2/2007 | Tom et al. |
| 2017/0312379 A1 | 11/2017 | Stibich |
| 2019/0022261 A1 | 1/2019 | Dayton |
| 2019/0030195 A1 | 1/2019 | Hatti et al. |
| 2019/0111169 A1 | 4/2019 | Flaherty et al. |

OTHER PUBLICATIONS

Moore, Samuel K., "Flight of the GermFalcon: How a Potential Coronavirus-Killing Airplane Sterilizer Was Born," Mar. 9, 2020, downloaded from: https://spectrum.ieee.org/tech-talk/aerospace/aviation/germfalcon-coronavirus-airplane-ultraviolet-sterilizer-news downloaded on Jul. 8, 2020.

Alcock, Charles, "UV-C Light System Eliminates Covid-19 from Aircraft Cabins," Apr. 27, 2020, https://www.ainonline.com/aviation-news/aerospace/2020-04-27/uv-c-light-system-eliminates-covid-19-aircraft-cabins.

Demaitre, Eugene, "Keenon Rolls Out Disinfection Robot to Hospitals in China and Beyond," May 1, 2020, https://www.therobotreport.com/keenon-rolls-out-disinfection-robot-china-covid-19/.

UVD Robots Infection Prevention downloaded from http://www.uvd-robots.com/ on Jul. 8, 2020.

\* cited by examiner

SYSTEM AND METHOD FOR CONTROLLING A UVC BASED AIRCRAFT SANITIZATION SYSTEM

CROSS REFERENCE TO RELATED APPLICATION

This application claims priority to Indian Provisional Patent Application No. 202011032291, filed Jul. 28, 2020, the entire content of which is incorporated by reference herein.

TECHNICAL FIELD

Embodiments of the subject matter described herein relate generally to UVC sanitization systems. More particularly, embodiments of the subject matter relate to control systems for UVC sanitization systems.

BACKGROUND

Due to the potential for aircraft passengers and/or crew to expose aircraft surfaces to various pathogens during flight, aircraft cabin surfaces UVC (ultra violet C) sanitization units have been proposed. The UVC sanitation units can direct UVC radiation at a target surface in an attempt to kill harmful pathogens on the target surface. Current UVC sanitization units utilize an open loop control of UV radiation. Because open loop control is utilized, the UV radiation received at a target surface from the current UVC sanitation units will change based on varying operating conditions, even when the radiation emitted by the source remains constant. Thus, the effectiveness of surface sanitization using the current UVC sanitation units will also vary with the varying operating conditions.

Hence, it is desirable to provide a consistent and effective closed loop control of a UVC sanitization system. Furthermore, other desirable features and characteristics of the present invention will become apparent from the subsequent detailed description and the appended claims, taken in conjunction with the accompanying drawings and the foregoing technical field and background.

SUMMARY

This summary is provided to describe select concepts in a simplified form that are further described in the Detailed Description. This summary is not intended to identify key or essential features of the claimed subject matter, nor is it intended to be used as an aid in determining the scope of the claimed subject matter.

In one embodiment, a control system in a UVC-based aircraft sanitization system for controlling the UVC-based aircraft sanitization system to maintain a desired UVC (ultraviolet C) radiation level at a target surface in an aircraft under varying operating conditions is disclosed. The control system includes a controller configured to: receive sensor feedback from a sensor that measures a property from which a radiation level that is applied at the target surface by the UVC-based aircraft sanitization system can be determined. The controller is further configured to generate a UVC source control command for UVC sources in the UVC-based aircraft sanitization system, based on the received sensor feedback, to control the UVC sources to increase or decrease radiation level output to generate sufficient radiation to achieve the desired radiation level at the target surface.

In another embodiment, a method for controlling a UVC-based aircraft sanitization system to maintain a desired UVC (ultraviolet C) radiation level at a target surface in an aircraft under varying operating conditions is provided. The method includes: receiving sensor feedback from one or more sensors that measure a property from which a radiation level that is applied at the target surface by the UVC-based aircraft sanitization system can be determined. The method further includes generating a UVC source control command for UVC sources in the UVC-based aircraft sanitization system, based on the received sensor feedback, to control the UVC sources to increase or decrease radiation level output to generate sufficient radiation to achieve the desired radiation level at the target surface.

In another embodiment, non-transitory computer readable media encoded with programming instructions configurable to cause a processor in a control system of a UVC-based aircraft sanitization system to perform a method is provided. The method includes: receiving sensor feedback from one or more sensors that measure a property from which a radiation level that is applied at the target surface by the UVC-based aircraft sanitization system can be determined. The method further includes generating a UVC source control command for UVC sources in the UVC-based aircraft sanitization system, based on the received sensor feedback, to control the UVC sources to increase or decrease radiation level output to generate sufficient radiation to achieve a desired radiation level at the target surface.

In another embodiment, a control system in a UVC-based aircraft sanitization system for controlling the UVC-based aircraft sanitization system to maintain a desired UVC (ultraviolet C) radiation level at a target surface in an aircraft under varying operating conditions is disclosed. The control system includes a controller configured to: receive measured radiation feedback from a radiation measurement device (e.g., dosimeter) on the target surface that identifies a radiation level that is applied at the target surface by the UVC-based aircraft sanitization system; and generate a UVC source control command for UVC sources in the UVC-based aircraft sanitization system, based on the received measured radiation feedback, to control the UVC sources to increase or decrease radiation level output (e.g., identify the amount of increase or decrease from the UVC sources) to generate sufficient radiation to achieve the desired radiation level at the target surface.

In another embodiment, a method for controlling a UVC-based aircraft sanitization system to maintain a desired UVC (ultraviolet C) radiation level at a target surface in an aircraft under varying operating conditions is disclosed. The method includes: receiving measured radiation feedback from an radiation measurement device (e.g., dosimeter) on the target surface that identifies a radiation level that is applied at the target surface by the UVC-based aircraft sanitization system; and generating a UVC source control command for UVC sources in the UVC-based aircraft sanitization system, based on the received measured radiation feedback, to control the UVC sources to increase or decrease radiation level output (e.g., identify the amount of increase or decrease from the UVC sources) to generate sufficient radiation to achieve the desired radiation level at the target surface.

In another embodiment, non-transitory computer readable media encoded with programming instructions configurable to cause a processor in the control system of a UVC-based aircraft sanitization system to perform a method is provided. The method including: receiving measured radiation feedback from a radiation measurement device (e.g., dosimeter)

on the target surface that identifies a radiation level that is applied at the target surface by the UVC-based aircraft sanitization system; and generating a UVC source control command for UVC sources in the UVC-based aircraft sanitization system. based on the received measured radiation feedback, to control the UVC sources to increase or decrease radiation level output (e.g., identify the amount of increase or decrease from the UVC sources) to generate sufficient radiation to achieve the desired radiation level at the target surface.

Furthermore, other desirable features and characteristics will become apparent from the subsequent detailed description and the appended claims, taken in conjunction with the accompanying drawings and the preceding background.

BRIEF DESCRIPTION OF THE DRAWINGS

Embodiments of the subject matter will hereinafter be described in conjunction with the following drawing figures, wherein like numerals denote like elements, and wherein.

DETAILED DESCRIPTION

Figure 1:
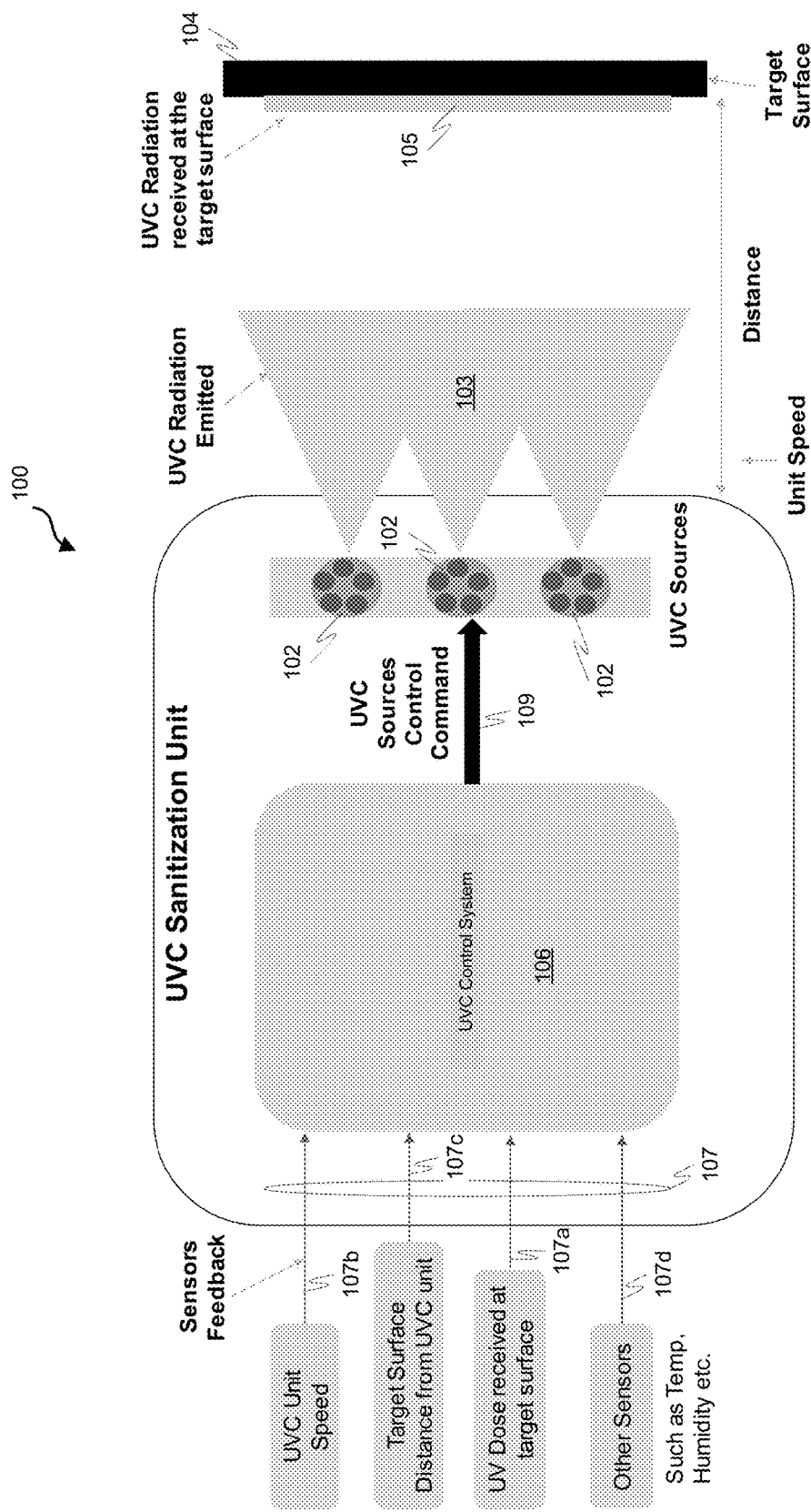
FIG. 1 is a block diagram depicting an example UVC sanitation system, in accordance with some embodiments.

The following detailed description is merely exemplary in nature and is not intended to limit the application and uses. Furthermore, there is no intention to be bound by any expressed or implied theory presented in the preceding technical field, background, summary, or the following detailed description. As used herein, the term "module" refers to any hardware, software, firmware, electronic control component, processing logic, and/or processor device, individually or in any combination, including without limitation: application specific integrated circuit (ASIC), a field-programmable gate-array (FPGA), an electronic circuit, a processor (shared, dedicated, or group) and memory that executes one or more software or firmware programs, a combinational logic circuit, and/or other suitable components that provide the described functionality.

Embodiments of the present disclosure may be described herein in terms of functional and/or logical block components and various processing steps. It should be appreciated that such block components may be realized by any number of hardware, software, and/or firmware components configured to perform the specified functions. For example, an embodiment of the present disclosure may employ various integrated circuit components, e.g., memory elements, digital signal processing elements, logic elements, look-up tables, or the like, which may carry out a variety of functions under the control of one or more microprocessors or other control devices. In addition, those skilled in the art will appreciate that embodiments of the present disclosure may be practiced in conjunction with any number of systems, and that the systems described herein is merely exemplary embodiments of the present disclosure.

For the sake of brevity, conventional techniques related to signal processing, data transmission, signaling, control, and other functional aspects of the systems (and the individual operating components of the systems) may not be described in detail herein. Furthermore, the connecting lines shown in the various figures contained herein are intended to represent example functional relationships and/or physical couplings between the various elements. It should be noted that many alternative or additional functional relationships or physical connections may be present in an embodiment of the present disclosure.

The subject matter described herein discloses apparatus, systems, techniques and articles for providing a controller that will endeavor to maintain a desired UV radiation level at a target surface, under varying operating conditions, such as sanitization unit speed variations, UVC source degradation over operating life, varying distance between the UVC unit and the target surface, and others. The apparatus, systems, techniques and articles provided receive feedback from various sensors and, based on the received feedback, generate a control command for the UVC sources to cause the desired radiation level at the target surface to be achieved. The apparatus, systems, techniques and articles provided may also provide recommendations/adjustments such as: changing the speed of UVC sanitization unit, changing the distance between the UVC source and target surface, alerting when UVC sources are degraded, and others. The apparatus, systems, techniques and articles provided may provide recommendations to an operator in the case of manual operation of a UVC sanitization unit and control signals to affect adjustments in the case of autonomous UVC sanitization unit operation. The apparatus, systems, techniques and articles provided may provide an alert when the controller determines that the desired radiation level at the target surface is not achievable.

FIG. 1 is a block diagram depicting an example UVC sanitation system 100. The example UVC sanitation system 100 includes a plurality of UVC sources 102 for emitting UVC radiation 103 for irradiating a target surface 104 with UVC radiation 105. The example UVC sanitation system 100 includes a UVC control system 106 for controlling the UVC sources 102 to emit sufficient radiation to irradiate the target surface 104 with a desired UVC radiation level. The example UVC control system 106 includes a plurality of inputs for receiving sensor feedback 107 from a plurality of sensors (e.g., dosimeter, speedometer, range finder, thermometer, humidity sensor, and others) that provide feedback regarding the UV dose received at the target surface (feedback 107a), UVC unit speed (feedback 107b), distance from UVC sources to target surface (feedback 107c), and environmental conditions such as temperature and humidity (feedback 107d). The UVC control system 106 is configured to process the sensor feedback 107 to generate a UVC sources control command 109 to control the level of radiation emitted by the UVC sources 102.

The UVC control system 106 includes a controller that includes at least one processor and a computer-readable storage device or media encoded with programming instructions for configuring the controller. The processor may be any custom-made or commercially available processor, a central processing unit (CPU), a graphics processing unit (GPU), an application specific integrated circuit (ASIC), a field programmable gate array (FPGA), an auxiliary processor among several processors associated with the controller, a semiconductor-based microprocessor (in the form of a microchip or chip set), any combination thereof, or generally any device for executing instructions.

The computer readable storage device or media may include volatile and nonvolatile storage in read-only memory (ROM), random-access memory (RAM), and keep-alive memory (KAM), for example. KAM is a persistent or non-volatile memory that may be used to store various operating variables while the processor is powered down. The computer-readable storage device or media may be implemented using any of a number of known memory devices such as PROMs (programmable read-only memory), EPROMs (electrically PROM), EEPROMs (electrically erasable PROM), flash memory, or any other electric, magnetic, optical, or combination memory devices capable of storing data, some of which represent executable programming instructions, used by the controller.

The controller in the control system 106 is configured to receive measured radiation feedback 107a from a radiation measurement device (e.g., dosimeter) on the target surface 104 that identifies a radiation level that is applied at the target surface 104 by the UVC-based aircraft sanitization system 100. The controller is configured to receive speed feedback 107b from a speed measurement device (e.g., speedometer) that measures the speed at which the UVC-based aircraft sanitization system 100 travels while irradiating the target surface 104. The controller is configured to receive distance feedback from a distance measurement device (e.g., range finder) that measures the distance between the UVC-based aircraft sanitization system 100 and the target surface 104 while the target surface 104 is being irradiated.

The controller is configured to generate a speed control command (for an operator or for controlling movement in robotic mode), based on the received speed feedback 107b, that identifies a level of speed increase or speed decrease for the UVC-based aircraft sanitization system 100 to achieve the desired radiation level at the target surface 104. The controller is configured to generate a distance control command (for an operator or for controlling movement in robotic/autonomous operating mode mode), based on the received distance feedback, that identifies a level of distance increase or distance decrease for the UVC-based aircraft sanitization system 100 to achieve the desired radiation level at the target surface 104. The controller is configured to generate the UVC source control command 109 for UVC sources 102 in the UVC-based aircraft sanitization system 100, based on the received measured radiation feedback 107a, the distance feedback 107c, and the speed feedback 107b, to control the UVC sources 102 to increase or decrease radiation level output (e.g., identify the amount of increase or decrease from the UVC sources 102) to generate sufficient radiation to achieve the desired radiation level at the target surface 104.

The controller is optionally configured to receive environmental conditions feedback 107d from one or more environmental sensors (e.g., thermometer and humidity sensor) that measure environmental conditions including one or more of temperature and humidity and generate the UVC source control command 109 for UVC sources 102 in the UVC-based aircraft sanitization system 100, based on the received measured radiation feedback 107a, the distance feedback 107c, the speed feedback 107b, and the environmental conditions feedback 107d, to control the UVC sources 102 to increase or decrease radiation level output to generate sufficient radiation to achieve the desired radiation level at the target surface 104.

The controller is optionally configured to provide various messages to an operator of the UVC-based aircraft sanitization system 100. The messages may include a distance message comprising, for example, move closer or current distance is OK (e.g., based on a distance error); a speed message comprising, for example, slow down/or can move faster (e.g., based on a speed error); a radiation message comprising, for example, insufficient UV radiation or radiation OK (e.g., based on a dose error); and/or a change UV lamp message when the controller determines that a UV lamp needs to be changed.

The controller may operate according to the following high level control laws that may govern the UV radiation at the target surface. The controller may operate according to a UVC unit speed control law wherein the UV radiation received at the target surface is an inverse linear function of UVC unit speed whereby the higher the speed of the UVC unit, the lower the UVC radiation received at the target surface and the lower the speed of the UVC unit, the higher the UVC radiation received at the target surface. The controller may operate according to a UVC unit distance control law wherein the UV radiation received at the target surface is an inverse function of UVC unit distance (and typically an inverse square function) whereby (assuming the received radiation is orthogonal to the target surface) the further away the UVC unit is from the target surface, the lower the UVC radiation received at the target surface and the closer the UVC unit is to the target surface, the higher the UVC radiation received at the target surface. The controller may operate according to temperature and humidity control laws wherein a pathogen may be more stable at a lower temperature and a lower humidity level as compared to higher humidity and warmer environment. Based on the temperature and humidity feedback 107d, the controller may automatically adjust emitted UV radiation levels.

The controller may optionally be configured to determine, based on the received radiation, distance, speed, and/or environmental conditions feedback whether one or more of the UVC sources may be degraded and provide an indication that indicates that one or more of the UVC sources are degraded when it may be determined that one or more of the UVC sources are degraded. The indication may be in the form of a visual or audible message. The controller may be configured to determine whether one or more of the UVC sources 102 is degraded by comparing radiation levels measured at the target surface 104 with an expected radiation level at the target surface 104 determined based on the a level of output commanded via the UVC source control command 109 and one or more of the level of speed commanded via the speed control command and the level of distance commanded via the distance control command. The controller may be further configured to generate a warning message indicating insufficient sanitization when the desired radiation level at the target surface may be not achievable through commands by the controller to adjust the radiation emitted by the UVC sources, adjust the speed of the UVC-based aircraft sanitization system up or down and/or adjust the path of the UVC-based aircraft sanitization system closer or further away from the target surface.

Figure 2:
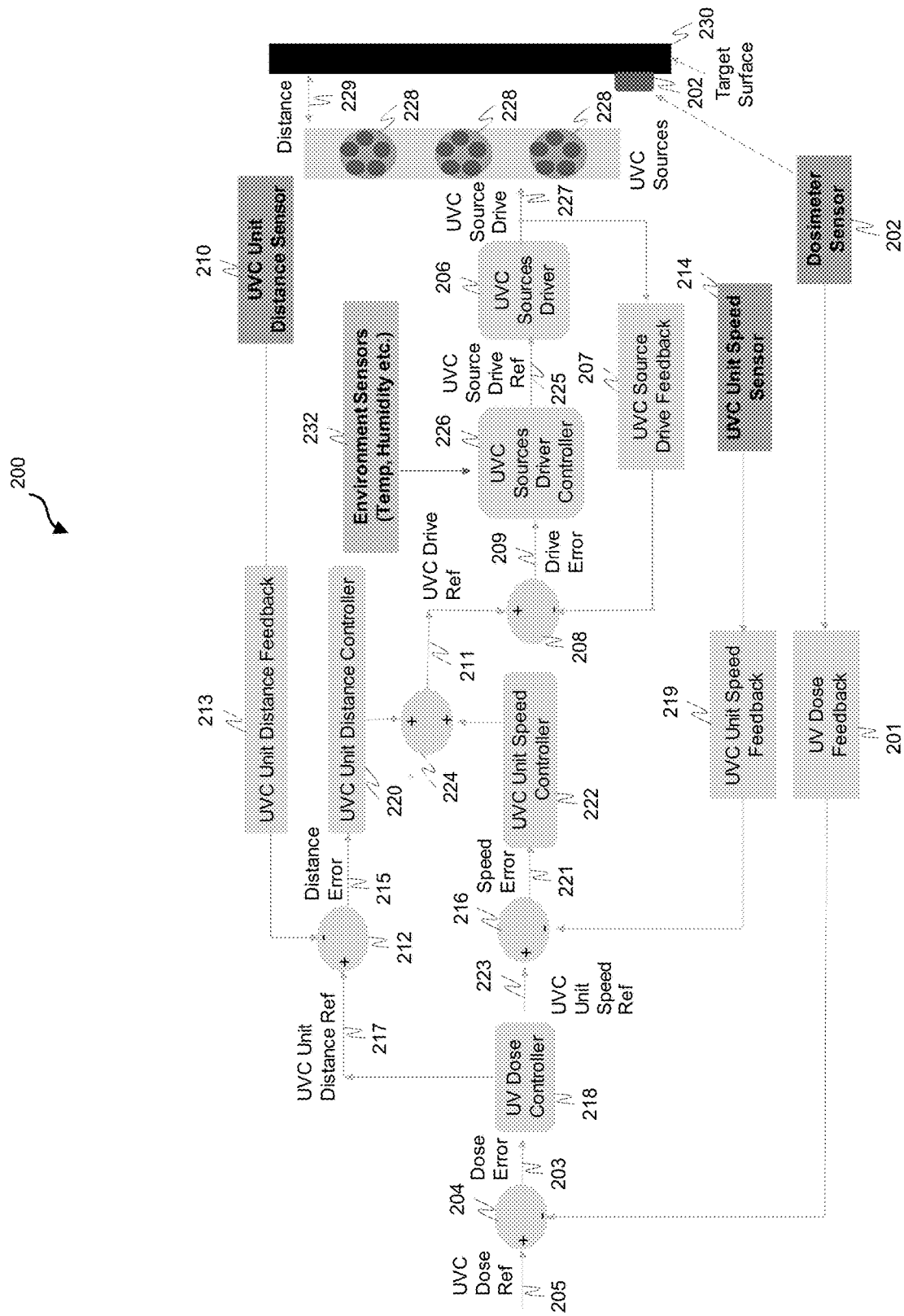
FIG. 2 is a block diagram depicting an example control system, in accordance with some embodiments.

FIG. 2 is a block diagram depicting an example control system 200. The control system 200 includes: an outer feedback loop for receiving UV dose feedback 201 from a radiation measurement device 202 (e.g., dosimeter) on a target surface 230 and generating a dose error 203 based on a comparison of a UVC dose reference 205 with the UV dose feedback 201 via an adder 204; an inner feedback loop for receiving UVC source drive feedback 207 from a UVC source driver 206 and generating a drive error 209 based on a comparison of a UVC drive reference 211 with the UVC source drive feedback 207 via an adder 208 and ultimately a UVC source control command 227 for the UVC sources 228, based on the dose error 203 and the UVC source drive feedback 207, to control the UVC sources 228 to increase or decrease radiation level output; a first intermediate feedback loop between the outer feedback loop and the inner feedback loop for receiving UVC distance feedback 213 from a UVC unit distance sensor 210 and generating a distance error 215 based on a comparison of a UVC distance reference 217 with the UVC distance feedback 213 via an adder 212; and a second intermediate feedback loop between the outer feedback loop and the inner feedback loop for receiving UVC unit speed feedback 219 from a UVC unit speed sensor 214 and generating a speed error 221 based on a comparison of a UVC speed reference 223 with the unit speed feedback 219 via an adder 216. The UVC unit speed sensor 214 measures the speed at which the UVC unit travels while irradiating the target surface 230.

The example control system 200 includes a UV dose controller 218 for generating the UVC distance reference 217 and the UVC unit speed reference 223 from the dose error 203. The example control 220 further includes a UVC speed controller 222 and a UVC distance controller 220, each of which generates signals that are added to each other in an adder 224 to generate the UVC drive reference 211.

The example control system 200 includes a UVC source driver controller 226 which receives the drive error 209 and generates a UVC source drive reference 225 based on the drive error 209. The UVC source driver 206 generates a UVC source drive command 227 and the UVC source drive feedback 207 based on the UVC source drive reference 225. The UVC source drive command 227 controls individual sources in the UVC sources 228 to output a desired level of UVC radiation emissions. The UVC source driver controller 226 may optionally receive feedback from environment sensors 232 (e.g., temperature, humidity, and other sensors) and generate the UVC source drive reference 225 based on the drive error 209 and the feedback from environment sensors 232.

The UVC unit distance sensor measures the distance 229 between the UVC sources 228 and the target surface 230 and provides the UVC unit distance feedback. The radiation measurement device 202 (e.g., dosimeter) is mounted to the target surface 230, measures the radiation experienced at the target surface and provides the UV dose feedback 201. Although only one radiation measurement device 202 (e.g., dosimeter) is shown, it is contemplated that the target surface 230 would have multiple devices 202 at multiple locations along the target surface 230.

The dose error 203 is used to generate the UVC unit distance reference 217 used in the first intermediate feedback loop to generate the distance error 215. The dose error 203 is used to generate the UVC speed unit reference 223 used in the second intermediate feedback loop to generate the speed error 221. The distance error 215 and the speed error 221 are used to generate a UVC drive reference 211 used in the inner loop to generate the drive error 209. The drive error 209 is used to generate the UVC source drive reference 225 for generating the control command 227 for the UVC sources 228. Also, the UVC unit distance reference 217 may be used to provide an operator of the UVC-based aircraft sanitization system with a distance message, for example, move closer or current distance is OK (e.g., based on a distance error 215). Additionally, the UVC speed unit reference 223 may be used to provide an operator of the UVC-based aircraft sanitization system with a speed message, for example, slow down/or can move faster (e.g., based on the speed error 221).

The example control system 200 is optionally configured to receive environmental conditions feedback from one or more environmental sensors 232 that measure environmental conditions including one or more of temperature and humidity and generate the UVC source control command 227 for UVC sources 228, based on the received measured radiation feedback 201, the distance feedback 213, the speed feedback 219, and the environmental conditions feedback, to control the UVC sources 228 to increase or decrease radiation level output to generate sufficient radiation to achieve the desired radiation level at the target surface 230.

Figure 3:
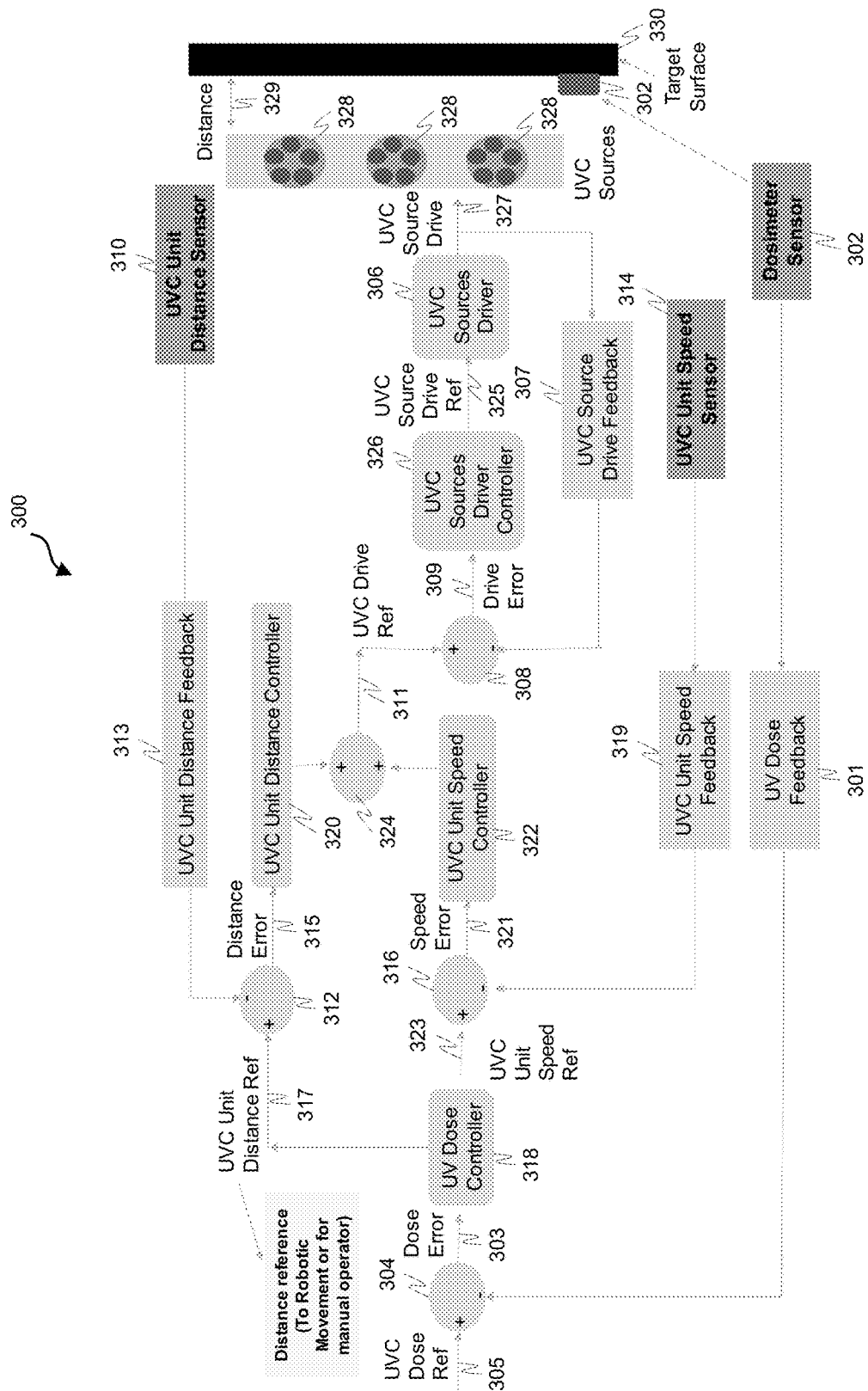
FIG. 3 is a block diagram depicting another example control system, in accordance with some embodiments.

FIG. 3 is a block diagram depicting another example control system 300. The control system 300 includes: an outer feedback loop for receiving UV dose feedback 301 from a radiation measurement device 302 (e.g., dosimeter) on a target surface 330 and generating a dose error 303 based on a comparison of a UVC dose reference 305 with the UV dose feedback 301 via an adder 304; an inner feedback loop for receiving UVC source drive feedback 307 from a UVC source driver 306 and generating a drive error 309 based on a comparison of a UVC drive reference 311 with the UVC source drive feedback 307 via an adder 308 and ultimately a UVC source control command 327 for the UVC sources 328, based on the dose error 303 and the UVC source drive feedback 307, to control the UVC sources 328 to increase or decrease radiation level output; a first intermediate feedback loop between the outer feedback loop and the inner feedback loop for receiving UVC distance feedback 313 from a UVC unit distance sensor 310 and generating a distance error 315 based on a comparison of a UVC distance reference 317 with the UVC distance feedback 313 via an adder 312; and a second intermediate feedback loop between the outer feedback loop and the inner feedback loop for receiving UVC unit speed feedback 319 from a UVC unit speed sensor 314 and generating a speed error 321 based on a comparison of a UVC speed reference 323 with the unit speed feedback 319 via an adder 316. The UVC unit speed sensor 314 measures the speed at which the UVC unit travels while irradiating the target surface 330.

The example control system 300 includes a UV dose controller 318 for generating the UVC distance reference 317 and the UVC unit speed reference 323 from the dose error 303. The example control 320 further includes a UVC speed controller 322 and a UVC distance controller 320, each of which generates signals that are added to each other in an adder 324 to generate the UVC drive reference 311.

The example control system 300 includes a UVC source driver controller 326 which receives the drive error 309 and generates a UVC source drive reference 325 based on the drive error 309. The UVC source driver 306 generates a UVC source drive command 327 and the UVC source drive feedback 307 based on the UVC source drive reference 325. The UVC source drive command 327 controls individual sources in the UVC sources 328 to output a desired level of UVC radiation emissions. Thus, the inner feedback loop is configured to generate the UVC source control command 327 for the UVC sources 328, based on the distance error 315, the speed error 321 and the UVC source drive feedback 307, to control the UVC sources to increase or decrease radiation level output.

The UVC unit distance sensor 310 measures the distance 329 between the UVC sources 328 and the target surface 330 and provides the UVC unit distance feedback 313. The radiation measurement device 302 (e.g., dosimeter) is mounted to the target surface 330, measures the radiation experienced at the target surface 330 and provides the UV dose feedback 301. Although only one radiation measurement device 302 (e.g., dosimeter) is shown, it is contemplated that the target surface 330 would have multiple devices 302 at multiple locations along the target surface 330.

The dose error 303 is used to generate the UVC unit distance reference 317 used in the first intermediate feedback loop to generate the distance error 315. The dose error 303 is used to generate the UVC speed unit reference 323 used in the second intermediate feedback loop to generate the speed error 321. The distance error 315 and the speed error 321 are used to generate a UVC drive reference 311 used in the inner loop to generate the drive error 309. The drive error 309 is used to generate the UVC source drive reference 325 for generating the control command 327 for the UVC sources 328. Also, the UVC unit distance reference 317 may be used to provide an operator of the UVC-based aircraft sanitization system with a distance message, for example, move closer or current distance is OK (e.g., based on a distance error 315). Additionally, the UVC speed unit reference 323 may be used to provide an operator of the UVC-based aircraft sanitization system with a speed message, for example, slow down/or can move faster (e.g., based on the speed error 321).

Figure 4:
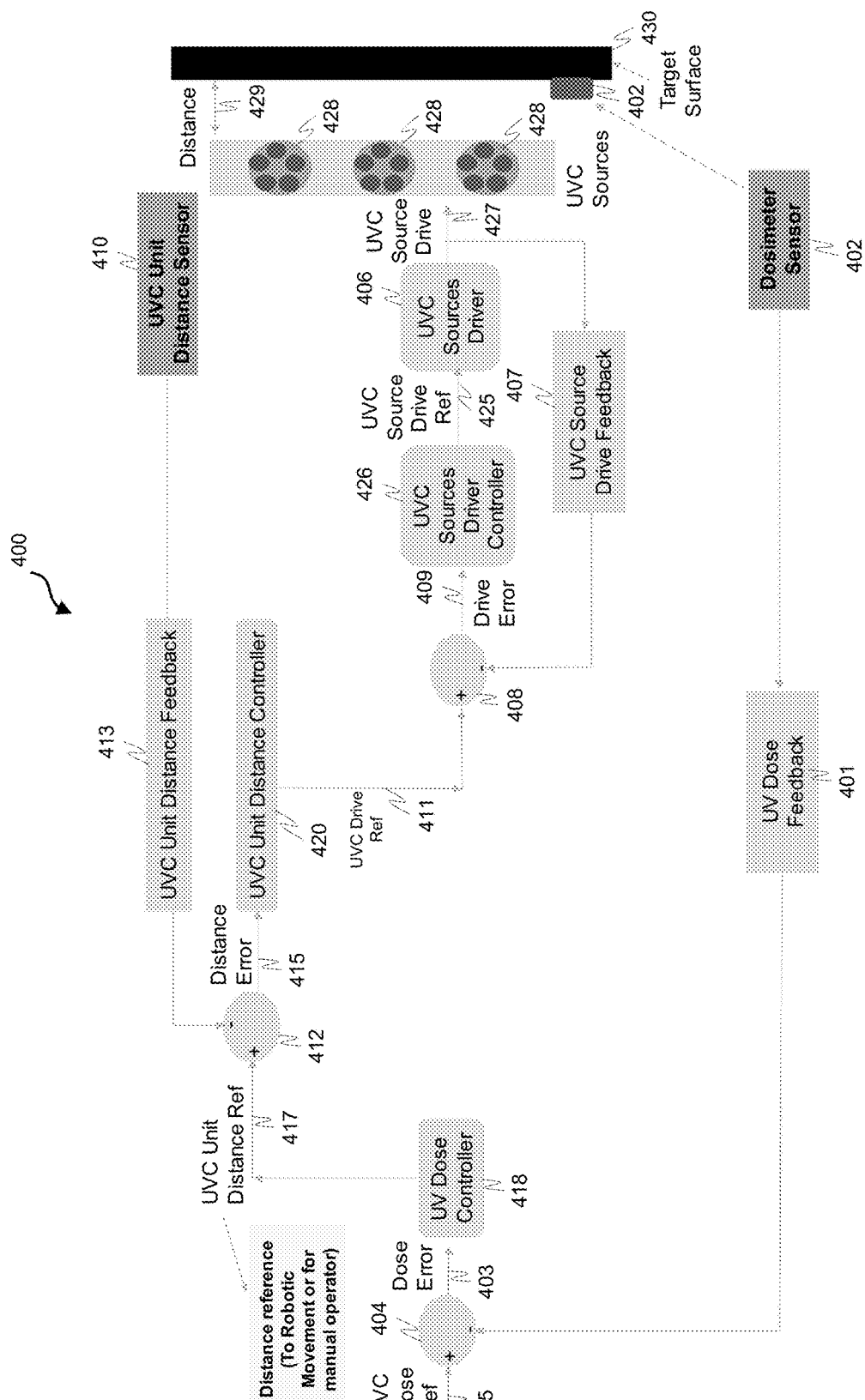
FIG. 4 is a block diagram depicting another example control system, in accordance with some embodiments.

FIG. 4 is a block diagram depicting another example control system 400. The control system 400 includes: an outer feedback loop for receiving UV dose feedback 401 from a radiation measurement device 402 (e.g., dosimeter) on a target surface 430 and generating a dose error 403 based on a comparison of a UVC dose reference 405 with the UV dose feedback 401 via an adder 404; an inner feedback loop for receiving UVC source drive feedback 407 from a UVC source driver 406 and generating a drive error 409 based on a comparison of a UVC drive reference 411 with the UVC source drive feedback 407 via an adder 408 and ultimately a UVC source control command 427 for the UVC sources 428, based on the dose error 403 and the UVC source drive feedback 407, to control the UVC sources 428 to increase or decrease radiation level output; and a first intermediate feedback loop between the outer feedback loop and the inner feedback loop for receiving UVC distance feedback 413 from a UVC unit distance sensor 410 and generating a distance error 415 based on a comparison of a UVC distance reference 417 with the UVC distance feedback 413 via an adder 412.

The example control system 400 includes a UV dose controller 418 for generating the UVC distance reference 417 from the dose error 403. The example control 420 further includes a UVC distance controller 420, which generates the UVC drive reference 411.

The example control system 400 includes a UVC source driver controller 426 which receives the drive error 409 and generates a UVC source drive reference 425 based on the drive error 409. The UVC source driver 406 generates a UVC source drive command 427 and the UVC source drive feedback 407 based on the UVC source drive reference 425. The UVC source drive command 427 controls individual sources in the UVC sources 428 to output a desired level of UVC radiation emissions. Thus, the inner feedback loop may be configured to generate the UVC source control command for the UVC sources, based on the distance error and the UVC source drive feedback, to control the UVC sources to increase or decrease radiation level output. The UVC source driver controller 426 may optionally receive feedback from environment sensors (e.g., temperature, humidity, and other sensors) and generate the UVC source drive reference 425 based on the drive error 409 and the feedback from environment sensors.

The UVC unit distance sensor 410 measures the distance 429 between the UVC sources 428 and the target surface 430 and provides the UVC unit distance feedback 413. The radiation measurement device 402 (e.g., dosimeter) is mounted to the target surface 430, measures the radiation experienced at the target surface 430 and provides the UV dose feedback 401. Although only one radiation measurement device 402 (e.g., dosimeter) is shown, it is contemplated that the target surface 430 would have multiple devices 402 at multiple locations along the target surface 430.

The dose error 403 is used to generate the UVC unit distance reference 417 used in the first intermediate feedback loop to generate the distance error 415. The distance error 415 is used to generate a UVC drive reference 411 used in the inner loop to generate the drive error 409. The drive error 409 is used to generate the UVC source drive reference 425 for generating the control command 427 for the UVC sources 428. Also, the UVC unit distance reference 417 may be used to provide an operator of the UVC-based aircraft sanitization system with a distance message, for example, move closer or current distance is OK (e.g., based on a distance error).

The example control system 400 is optionally configured to receive environmental conditions feedback from one or more environmental sensors that measure environmental conditions including one or more of temperature and humidity and generate the UVC source control command 427 for UVC sources 428, based on the UV dose feedback 401, the distance feedback 413, and the environmental conditions feedback, to control the UVC sources 428 to increase or decrease radiation level output to generate sufficient radiation to achieve the desired radiation level at the target surface 430.

Figure 5:
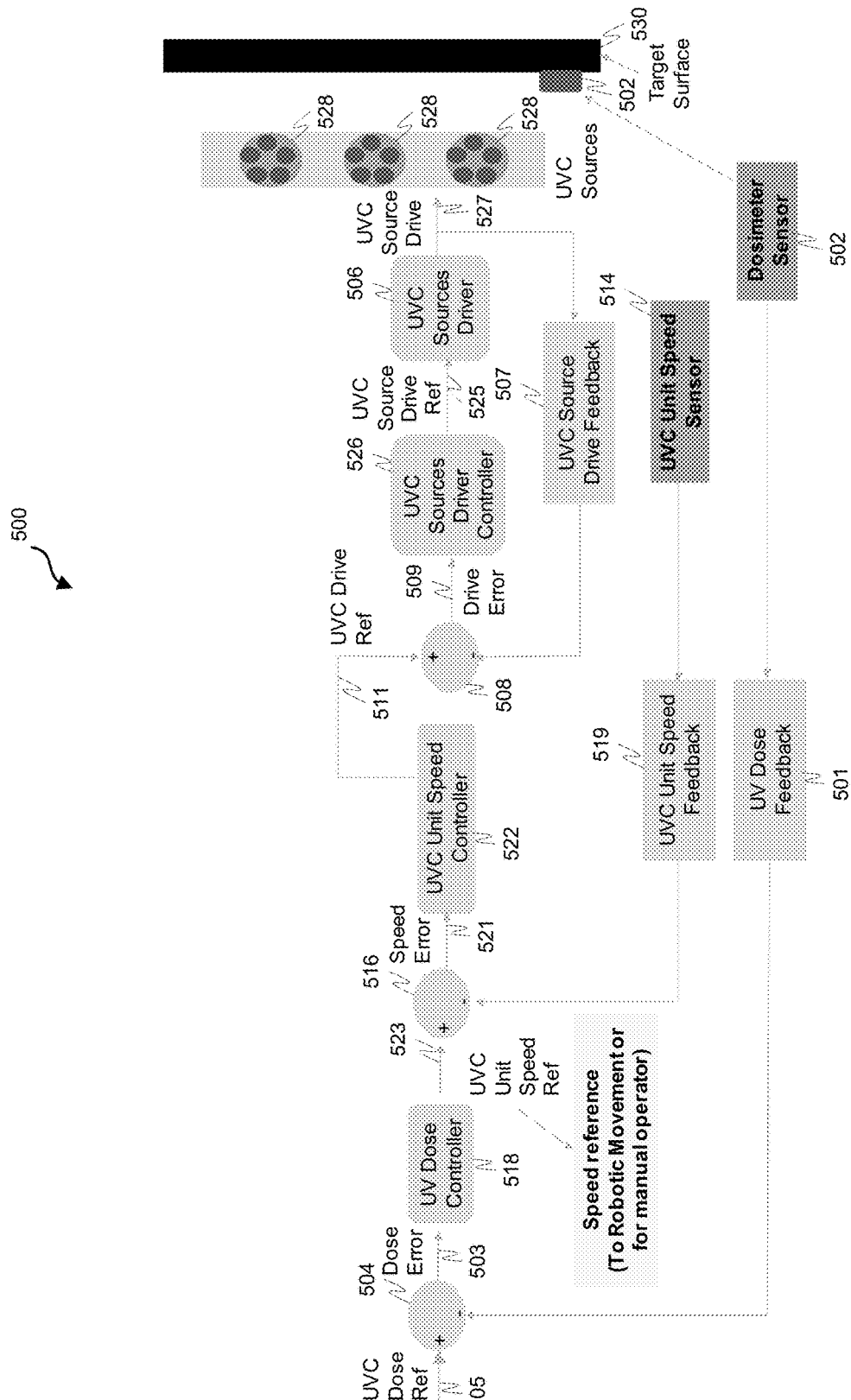
FIG. 5 is a block diagram depicting another example control system, in accordance with some embodiments.

FIG. 5 is a block diagram depicting another example control system 500. The control system 500 includes: an outer feedback loop for receiving UV dose feedback 501 from a radiation measurement device 502 (e.g., dosimeter) on a target surface 530 and generating a dose error 503 based on a comparison of a UVC dose reference 505 with the UV dose feedback 501 via an adder 504; an inner feedback loop for receiving UVC source drive feedback 507 from a UVC source driver 506 and generating a drive error 509 based on a comparison of a UVC drive reference 511 with the UVC source drive feedback 507 via an adder 508 and ultimately a UVC source control command 527 for the UVC sources 528, based on the dose error 503 and the UVC source drive feedback 507, to control the UVC sources 528 to increase or decrease radiation level output; and a second intermediate feedback loop between the outer feedback loop and the inner feedback loop for receiving UVC unit speed feedback 519 from a UVC unit speed sensor 514 and generating a speed error 521 based on a comparison of a UVC speed reference 523 with the unit speed feedback 519 via an adder 516. The UVC unit speed sensor 514 measures the speed at which the UVC unit travels while irradiating the target surface 530.

The example control system 500 includes a UV dose controller 518 for generating the UVC unit speed reference 523 from the dose error 503. The example control 520 further includes a UVC speed controller 522, which generates the UVC drive reference 511.

The example control system 500 includes a UVC source driver controller 526 which receives the drive error 509 and generates a UVC source drive reference 525 based on the drive error 509. The UVC source driver 506 generates a UVC source drive command 527 and the UVC source drive feedback 507 based on the UVC source drive reference 525. The UVC source drive command 527 controls individual sources in the UVC sources 528 to output a desired level of UVC radiation emissions. The UVC source driver controller 526 may optionally receive feedback from environment sensors (e.g., temperature, humidity, and other sensors) and generate the UVC source drive reference 525 based on the drive error 509 and the feedback from environment sensors.

The radiation measurement device 502 (e.g., dosimeter) is mounted to the target surface 530, measures the radiation experienced at the target surface and provides the UV dose feedback 501. Although only one radiation measurement device 502 (e.g., dosimeter) is shown, it is contemplated that the target surface 530 would have multiple devices 502 at multiple locations along the target surface 530.

The dose error 503 is used to generate the UVC speed unit reference 523 used in the second intermediate feedback loop to generate the speed error 521. The speed error 521 is used to generate a UVC drive reference 511 used in the inner loop to generate the drive error 509. The drive error 509 is used to generate the UVC source drive reference 525 for generating the control command 527 for the UVC sources 528. Also, the UVC speed unit reference 523 may be used to provide an operator of the UVC-based aircraft sanitization system with a speed message, for example, slow down/or can move faster (e.g., based on the speed error 521).

The example control system 500 is optionally configured to receive environmental conditions feedback from one or more environmental sensors that measure environmental conditions including one or more of temperature and humidity and generate the UVC source control command 527 for UVC sources 528, based on the UV dose feedback 501, the speed feedback 519, and the environmental conditions feedback, to control the UVC sources 528 to increase or decrease radiation level output to generate sufficient radiation to achieve the desired radiation level at the target surface 530.

Figure 6:
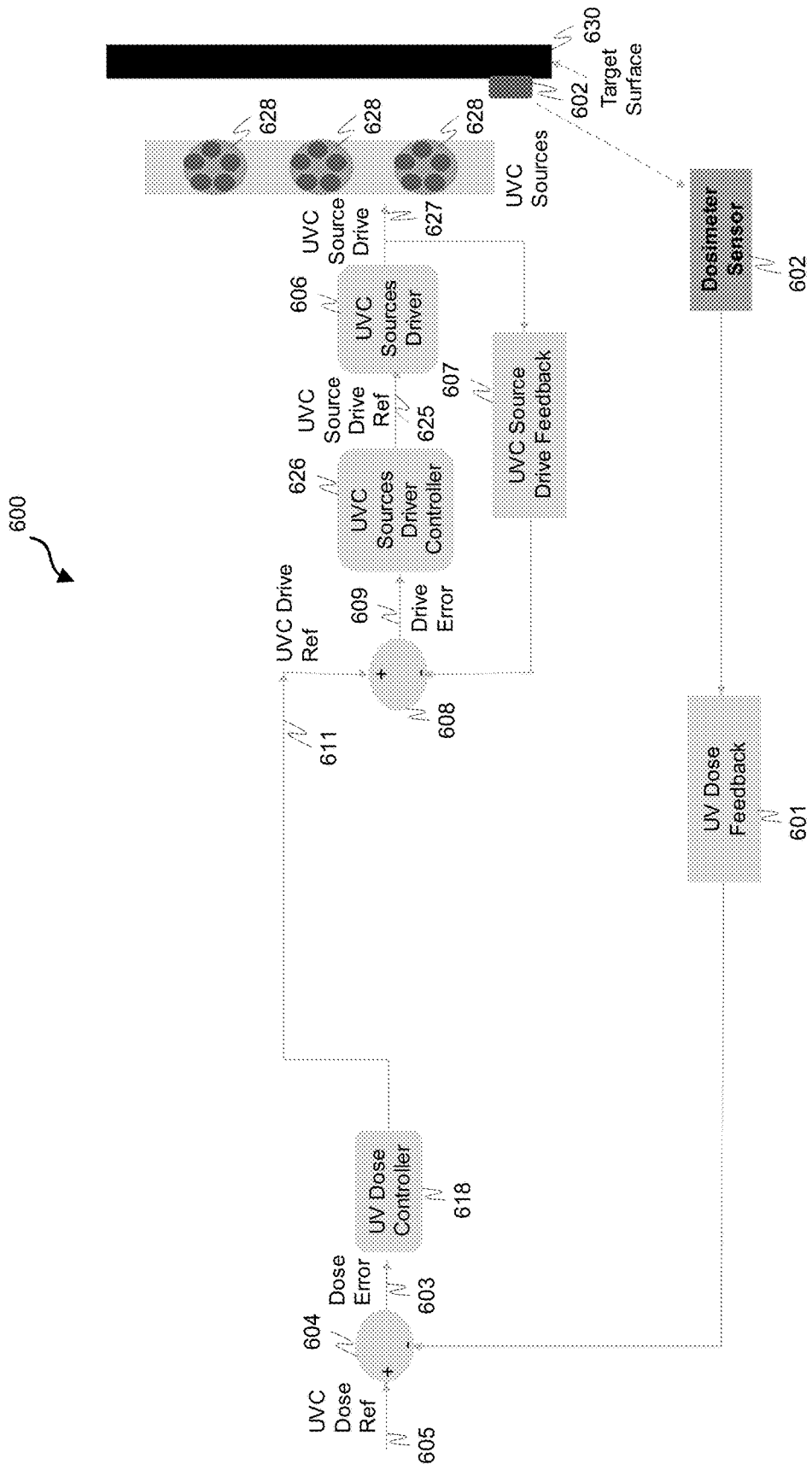
FIG. 6 is a block diagram depicting another example control system, in accordance with some embodiments.

FIG. 6 is a block diagram depicting another example control system 600. The control system 600 includes an outer feedback loop for receiving UV dose feedback 601 from a radiation measurement device 602 (e.g., dosimeter) on a target surface 630 and generating a dose error 603 based on a comparison of a UVC dose reference 605 with the UV dose feedback 601 via an adder 604; and an inner feedback loop for receiving UVC source drive feedback 607 from a UVC source driver 606 and generating a drive error 609 based on a comparison of a UVC drive reference 611 with the UVC source drive feedback 607 via an adder 608 and ultimately a UVC source control command 627 for the UVC sources 628, based on the dose error 603 and the UVC source drive feedback 607, to control the UVC sources 628 to increase or decrease radiation level output. The example control system 600 includes a UV dose controller 618 for generating the UVC drive reference 611.

The example control system 600 includes a UVC source driver controller 626 which receives the drive error 609 and generates a UVC source drive reference 625 based on the drive error 609. The UVC source driver 606 generates a UVC source drive command 627 and the UVC source drive feedback 607 based on the UVC source drive reference 625. The UVC source drive command 627 controls individual sources in the UVC sources 628 to output a desired level of UVC radiation emissions. The UVC source driver controller 626 may optionally receive feedback from environment sensors (e.g., temperature, humidity, and other sensors) and generate the UVC source drive reference 625 based on the drive error 609 and the feedback from environment sensors.

The radiation measurement device 602 (e.g., dosimeter) is mounted to the target surface 630, measures the radiation experienced at the target surface and provides the UV dose feedback 601. Although only one radiation measurement device 602 (e.g., dosimeter) is shown, it is contemplated that the target surface 630 would have multiple devices 602 at multiple locations along the target surface 630.

The dose error 603 is used to generate a UVC drive reference 611 used in the inner loop to generate the drive error 609, and the drive error 609 is used to generate the UVC source drive reference 625 for generating the control command 627 for the UVC sources 628.

The example control system 600 is optionally configured to receive environmental conditions feedback from one or more environmental sensors that measure environmental conditions including one or more of temperature and humidity and generate the UVC source control command 627 for UVC sources 628, based on the UV dose feedback 601 and the environmental conditions feedback, to control the UVC sources 628 to increase or decrease radiation level output to generate sufficient radiation to achieve the desired radiation level at the target surface 630.

Figure 7:
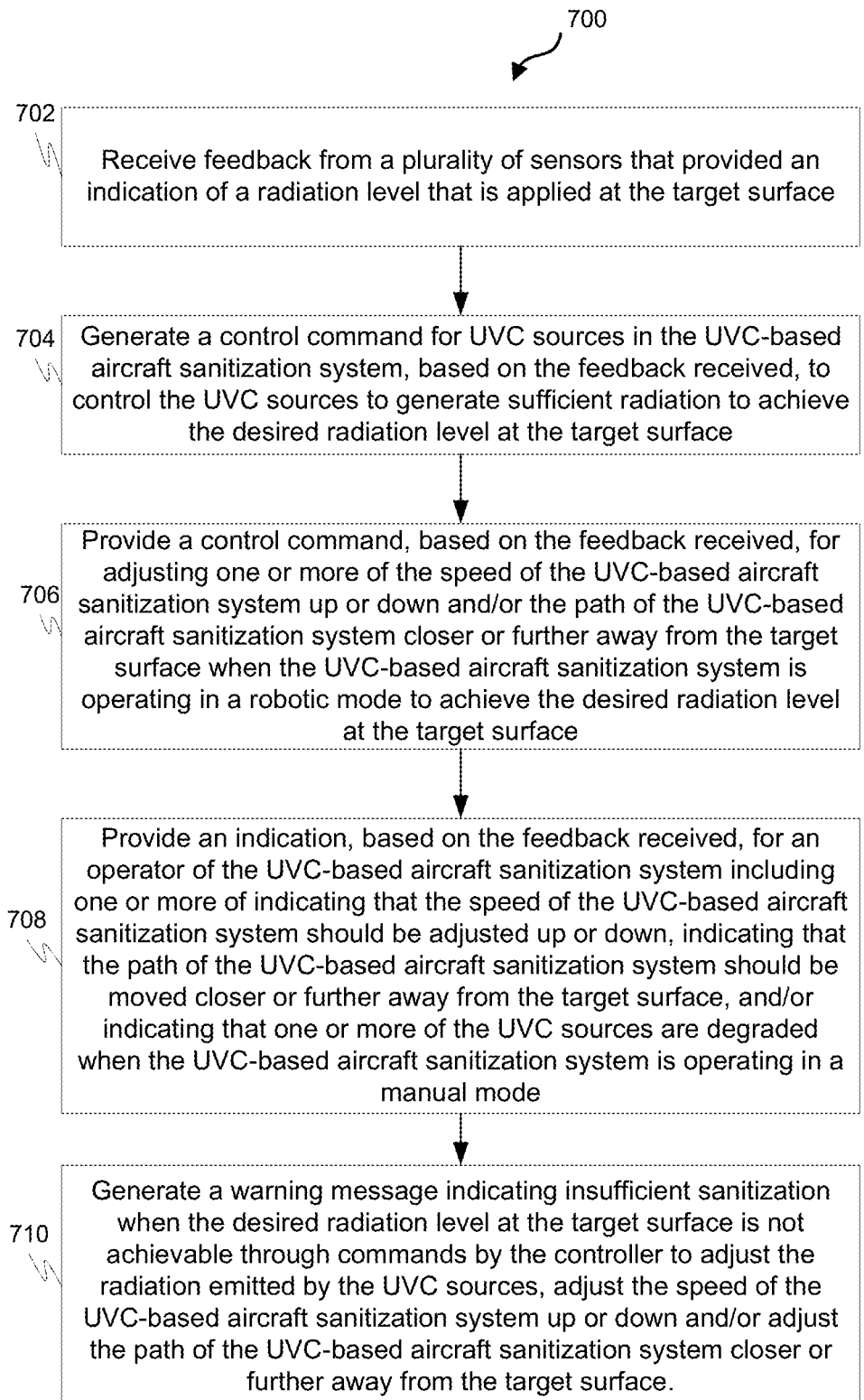
FIG. 7 is a process flow chart depicting an example process for controlling a UVC-based aircraft sanitization system to maintain a desired UVC radiation level at a target surface in an aircraft under varying operating conditions, in accordance with some embodiments.

FIG. 7 is a process flow chart depicting an example process 700 for controlling a UVC-based aircraft sanitization system to maintain a desired UVC radiation level at a target surface in an aircraft under varying operating conditions. The order of operation within the process 700 is not limited to the sequential execution as illustrated in the figure, but may be performed in one or more varying orders as applicable and in accordance with the present disclosure.

The example process 700 includes receiving feedback from a plurality of sensors that provided an indication of a radiation level that is applied at the target surface (operation 702). The sensors may include one or more of a speedometer, dosimeter, and rangefinder.

The example process 700 includes generating a control command for UVC sources in the UVC-based aircraft sanitization system, based on the feedback received, to control the UVC sources to generate sufficient radiation to achieve the desired radiation level at the target surface (operation 704).

The example process 700 optionally includes providing a control command, based on the feedback received, for adjusting one or more of the speed of the UVC-based aircraft sanitization system up or down and/or the path of the UVC-based aircraft sanitization system closer or further away from the target surface when the UVC-based aircraft sanitization system is operating in a robotic mode to achieve the desired radiation level at the target surface (operation 706).

The example process 700 optionally includes providing an indication, based on the feedback received, for an operator of the UVC-based aircraft sanitization system including one or more of indicating that the speed of the UVC-based aircraft sanitization system should be adjusted up or down, indicating that the path of the UVC-based aircraft sanitization system should be moved closer or further away from the target surface, and/or indicating that one or more of the UVC sources are degraded when the UVC-based aircraft sanitization system is operating in a manual mode (operation 708).

The example process 700 optionally includes generating a warning message indicating insufficient sanitization when the desired radiation level at the target surface is not achievable through commands by the controller to adjust the radiation emitted by the UVC sources, adjust the speed of the UVC-based aircraft sanitization system up or down and/or adjust the path of the UVC-based aircraft sanitization system closer or further away from the target surface. (operation 710).

Figure 8:
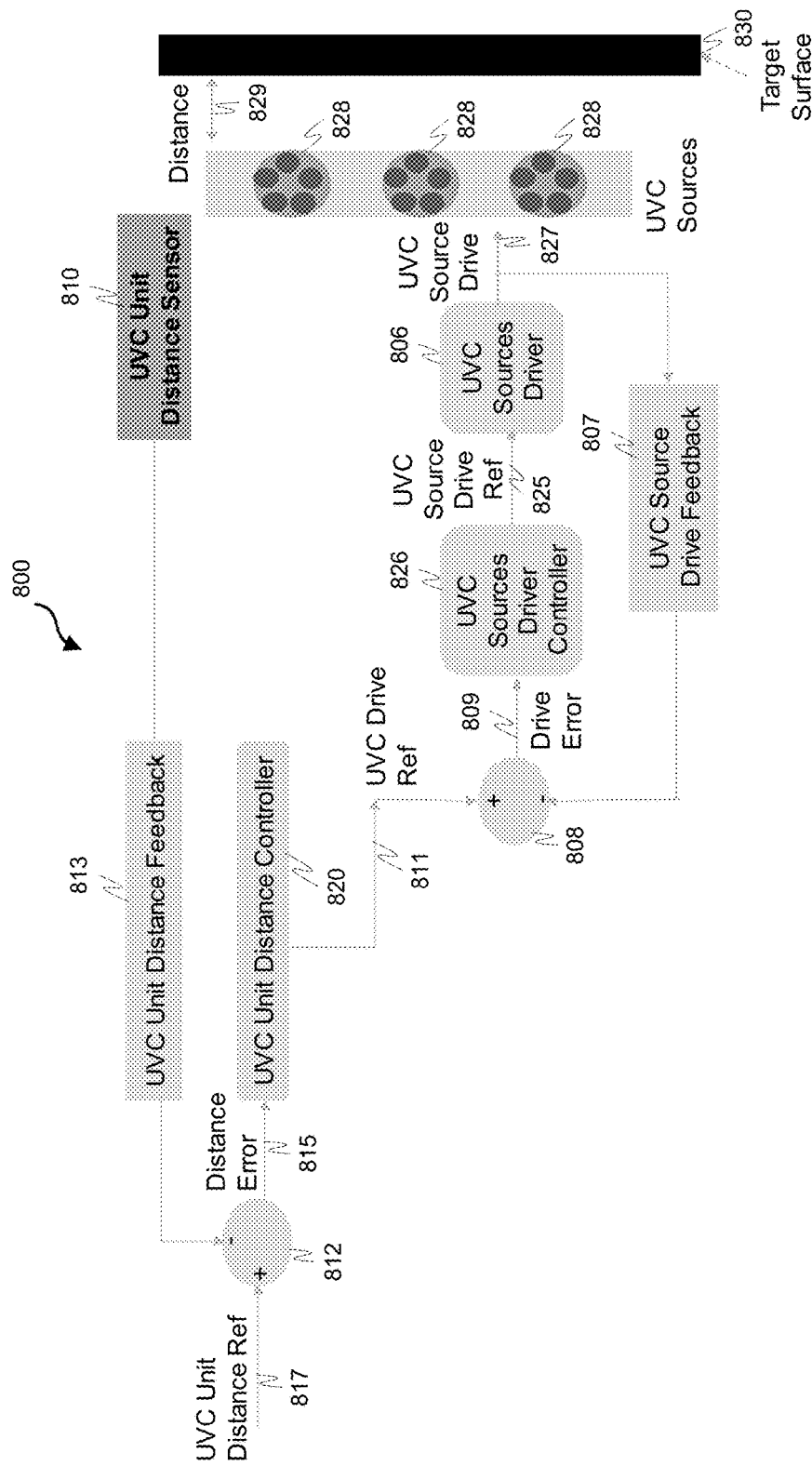
FIG. 8 is a block diagram depicting another example control system, in accordance with some embodiments.

FIG. 8 is a block diagram depicting another example control system 800. The control system 800 includes: an inner feedback loop for receiving UVC source drive feedback 807 from a UVC source driver 806 and generating a drive error 809 based on a comparison of a UVC drive reference 811 with the UVC source drive feedback 807 via an adder 808 and ultimately a UVC source control command 827 for the UVC sources 828, based on the dose the UVC source drive feedback 807, to control the UVC sources 828 to increase or decrease radiation level output; and a first intermediate feedback loop for receiving UVC distance feedback 813 from a UVC unit distance sensor 810 and generating a distance error 815 based on a comparison of a UVC distance reference 817 with the UVC distance feedback 813 via an adder 812. The example control 820 includes a UVC distance controller 820, which generates the UVC drive reference 811.

The example control system 800 includes a UVC source driver controller 826 which receives the drive error 809 and generates a UVC source drive reference 825 based on the drive error 809. The UVC source driver 806 generates a UVC source drive command 827 and the UVC source drive feedback 807 based on the UVC source drive reference 825. The UVC source drive command 827 controls individual sources in the UVC sources 828 to output a desired level of UVC radiation emissions. Thus, the inner feedback loop may be configured to generate the UVC source control command for the UVC sources, based on the distance error and the UVC source drive feedback, to control the UVC sources to increase or decrease radiation level output. The UVC source driver controller 826 may optionally receive feedback from environment sensors (e.g., temperature, humidity, and other sensors) and generate the UVC source drive reference 825 based on the drive error 809 and the feedback from environment sensors.

The UVC unit distance sensor 810 measures the distance 829 between the UVC sources 828 and the target surface 830 and provides the UVC unit distance feedback 813. The distance error 815 is used to generate a UVC drive reference 811 used in the inner loop to generate the drive error 809. The drive error 809 is used to generate the UVC source drive reference 825 for generating the control command 827 for the UVC sources 828. Also, the UVC unit distance reference 817 may be used to provide an operator of the UVC-based aircraft sanitization system with a distance message, for example, move closer or current distance is OK (e.g., based on a distance error).

The example control system 800 is optionally configured to receive environmental conditions feedback from one or more environmental sensors that measure environmental conditions including one or more of temperature and humidity and generate the UVC source control command 827 for UVC sources 828, based on the distance feedback 813 and the environmental conditions feedback, to control the UVC sources 828 to increase or decrease radiation level output to generate sufficient radiation to achieve the desired radiation level at the target surface 830.

Figure 9:
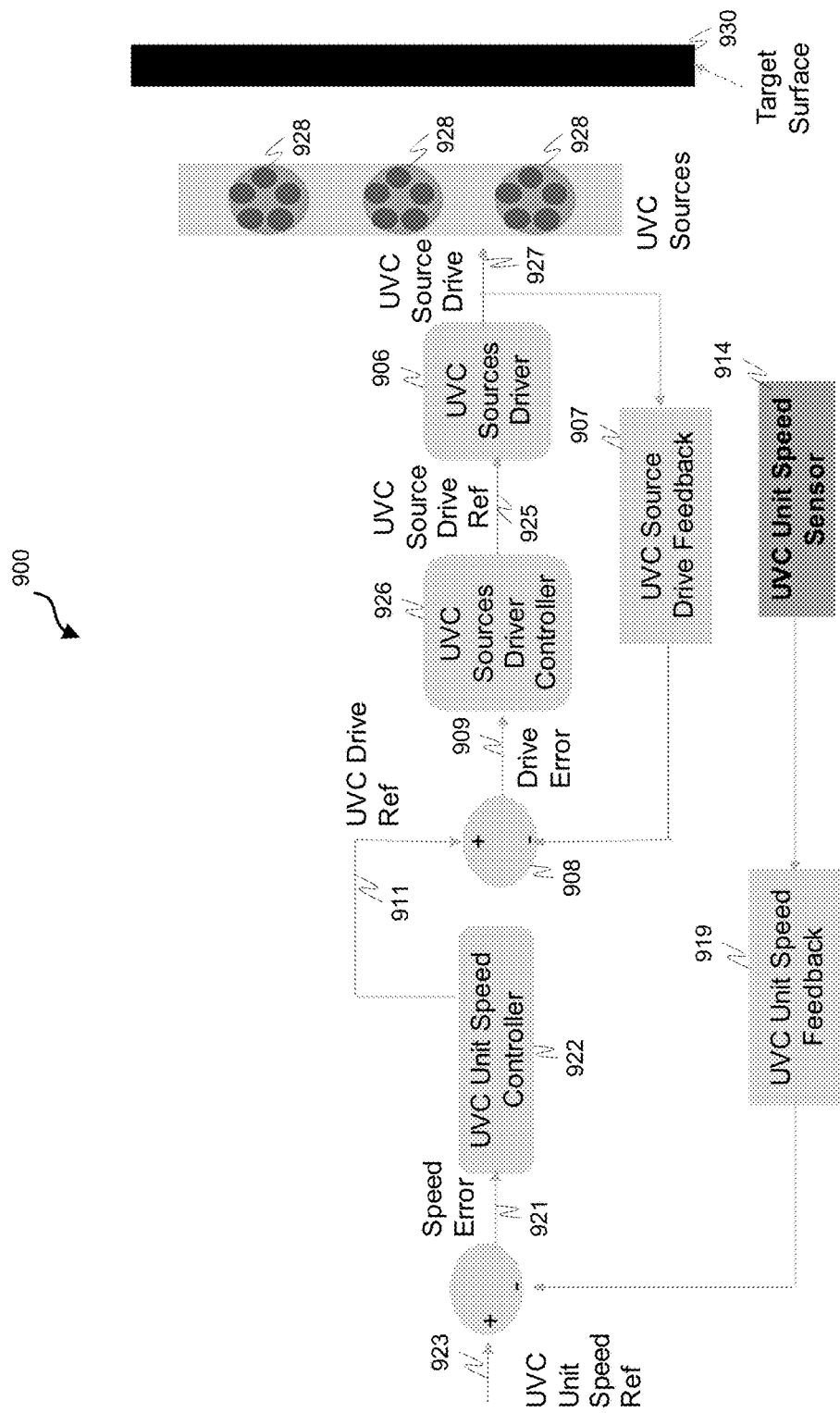
FIG. 9 is a block diagram depicting another example control system, in accordance with some embodiments.

FIG. 9 is a block diagram depicting another example control system 900. The control system 900 includes: an inner feedback loop for receiving UVC source drive feedback 907 from a UVC source driver 906 and generating a drive error 909 based on a comparison of a UVC drive reference 911 with the UVC source drive feedback 907 via an adder 908 and ultimately a UVC source control command 927 for the UVC sources 928, based on the UVC source drive feedback 907, to control the UVC sources 928 to increase or decrease radiation level output; and a second intermediate feedback loop for receiving UVC unit speed feedback 919 from a UVC unit speed sensor 914 and generating a speed error 921 based on a comparison of a UVC speed reference 923 with the unit speed feedback 919 via an adder 916. The example control 920 includes a UVC speed controller 922, which generates the UVC drive reference 911. The UVC unit speed sensor 914 measures the speed at which the UVC unit travels while irradiating a target surface 930.

The example control system 900 includes a UVC source driver controller 926 which receives the drive error 909 and generates a UVC source drive reference 925 based on the drive error 909. The UVC source driver 906 generates a UVC source drive command 927 and the UVC source drive feedback 907 based on the UVC source drive reference 925. The UVC source drive command 927 controls individual sources in the UVC sources 928 to output a desired level of UVC radiation emissions. The UVC source driver controller 926 may optionally receive feedback from environment sensors (e.g., temperature, humidity, and other sensors) and generate the UVC source drive reference 925 based on the drive error 909 and the feedback from environment sensors.

The speed error 921 is used to generate a UVC drive reference 911 used in the inner loop to generate the drive error 909. The drive error 909 is used to generate the UVC source drive reference 925 for generating the control command 927 for the UVC sources 928. Also, the UVC speed unit reference 923 may be used to provide an operator of the UVC-based aircraft sanitization system with a speed message, for example, slow down/or can move faster (e.g., based on the speed error 921).

The example control system 900 is optionally configured to receive environmental conditions feedback from one or more environmental sensors that measure environmental conditions including one or more of temperature and humidity and generate the UVC source control command 927 for UVC sources 928, based on the speed feedback 919 and the environmental conditions feedback, to control the UVC sources 928 to increase or decrease radiation level output to generate sufficient radiation to achieve the desired radiation level at the target surface 930.

Figure 10:
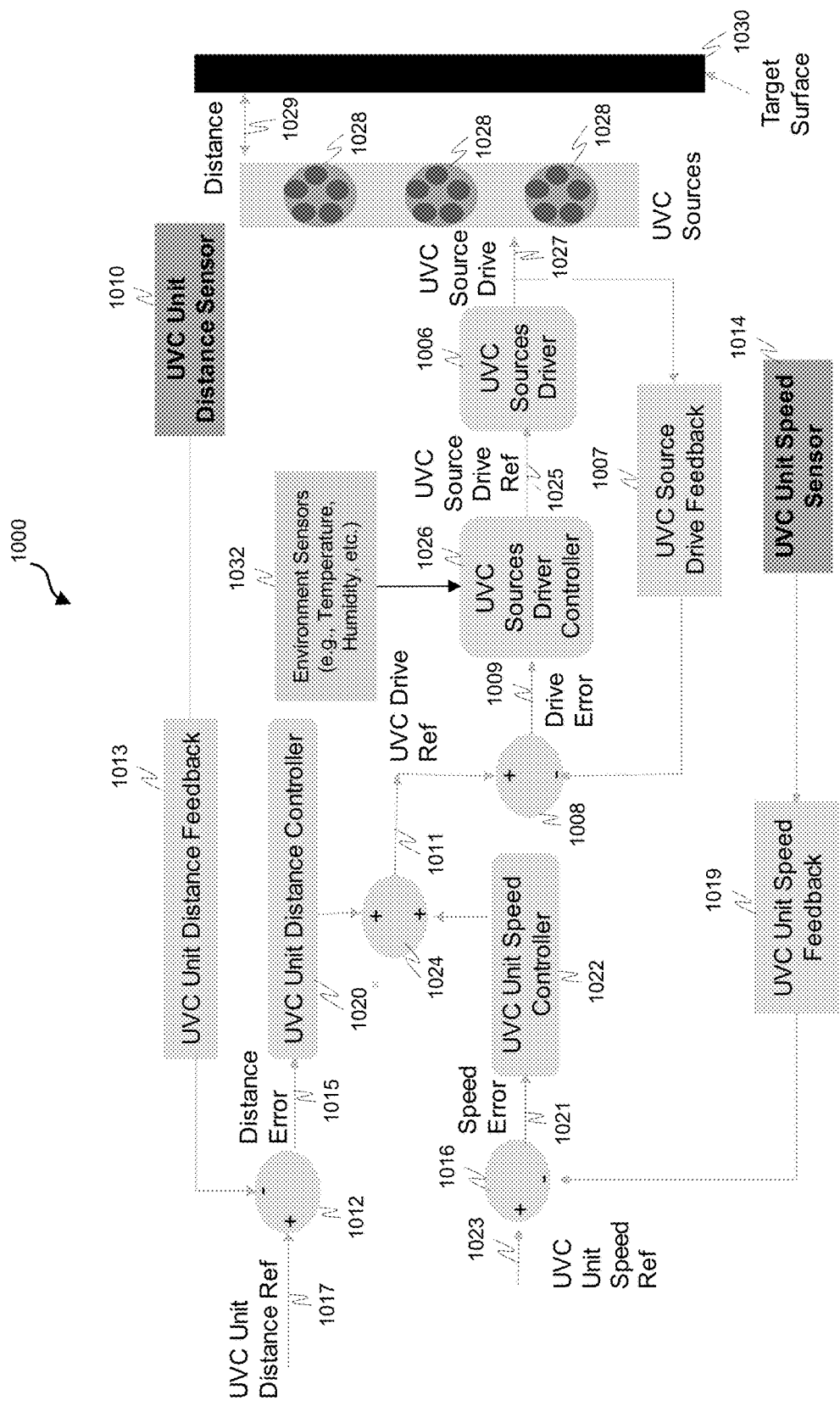
FIG. 10 is a block diagram depicting another example control system, in accordance with some embodiments.

FIG. 10 is a block diagram depicting another example control system 1000. The control system 1000 includes: an inner feedback loop for receiving UVC source drive feedback 1007 from a UVC source driver 1006 and generating a drive error 1009 based on a comparison of a UVC drive reference 1011 with the UVC source drive feedback 1007 via an adder 1008 and ultimately a UVC source control command 1027 for the UVC sources 1028, based on the UVC source drive feedback 1007, to control the UVC sources 1028 to increase or decrease radiation level output; a first intermediate feedback loop for receiving UVC distance feedback 1013 from a UVC unit distance sensor 1010 and generating a distance error 1015 based on a comparison of a UVC distance reference 1017 with the UVC distance feedback 1013 via an adder 1012; and a second intermediate feedback loop for receiving UVC unit speed feedback 1019 from a UVC unit speed sensor 1014 and generating a speed error 1021 based on a comparison of a UVC speed reference 1023 with the unit speed feedback 1019 via an adder 1016. The example control system 1000 further includes a UVC speed controller 1022 and a UVC distance controller 1020, each of which generates signals that are added to each other in an adder 1024 to generate the UVC drive reference 1011. The UVC unit distance sensor 1010 measures the distance 1029 between the UVC sources 1028 and the target surface 1030 and provides the UVC unit distance feedback. The UVC unit speed sensor 1014 measures the speed at which the UVC unit travels while irradiating the target surface 1030.

The example control system 1000 includes a UVC source driver controller 1026 which receives the drive error 1009 and generates a UVC source drive reference 1025 based on the drive error 1009. The UVC source driver 1006 generates a UVC source drive command 1027 and the UVC source drive feedback 1007 based on the UVC source drive reference 1025. The UVC source driver command 1027 controls individual sources in the UVC sources 1028 to output a desired level of UVC radiation emissions. The UVC source driver controller 1026 may optionally receive feedback from environment sensors (e.g., temperature, humidity, and other sensors) and generate the UVC source drive reference 1025 based on the drive error 1009 and the feedback from environment sensors 1032.

The distance error 1015 and the speed error 1021 are used to generate a UVC drive reference 1011 used in the inner loop to generate the drive error 1009. The drive error 1009 is used to generate the UVC source drive reference 1025 for generating the control command 1027 for the UVC sources 1028. Also, the UVC unit distance reference 1017 may be used to provide an operator of the UVC-based aircraft sanitization system with a distance message, for example, move closer or current distance is OK (e.g., based on a distance error 1015). Additionally, the UVC speed unit reference 1023 may be used to provide an operator of the UVC-based aircraft sanitization system with a speed message, for example, slow down/or can move faster (e.g., based on the speed error 1021).

The example control system 1000 is optionally configured to receive environmental conditions feedback from one or more environmental sensors that measure environmental conditions including one or more of temperature and humidity and generate the UVC source control command 1027 for UVC sources 1028, based on the distance feedback 1013, the speed feedback 1019, and the environmental conditions feedback, to control the UVC sources 1028 to increase or decrease radiation level output to generate sufficient radiation to achieve the desired radiation level at the target surface 1030.

Described herein are apparatus, systems, techniques and articles for providing a controller that will endeavor to maintain a desired UV radiation level at a target surface, under varying operating conditions. The apparatus, systems, techniques and articles provided receive feedback from one or more sensors and, based on the received feedback, generate a control command for the UVC sources to cause the desired radiation level at the target surface to be achieved.

In one embodiment, a control system in a UVC-based aircraft sanitization system for controlling the UVC-based aircraft sanitization system to maintain a desired UVC (ultraviolet C) radiation level at a target surface in an aircraft under varying operating conditions is provided. The control system comprises a controller configured to: receive sensor feedback from a sensor that measures a property from which a radiation level that is applied at the target surface by the UVC-based aircraft sanitization system can be determined; and generate a UVC source control command for UVC sources in the UVC-based aircraft sanitization system, based on the received sensor feedback, to control the UVC sources to increase or decrease radiation level output to generate sufficient radiation to achieve the desired radiation level at the target surface.

These aspects and other embodiments may include one or more of the following features. The sensor may comprise a radiation measurement device that measures the radiation that may be applied at the target surface; the sensor feedback may comprise measured radiation feedback that identifies a radiation level that may be applied at the target surface by the UVC-based aircraft sanitization system; and the controller may be configured to generate the UVC source control command for the UVC sources in the UVC-based aircraft sanitization system, based on the received measured radiation feedback and a referenced desired radiation level at the target surface, to control the UVC sources to increase or decrease radiation level output to generate sufficient radiation to achieve the desired radiation level at the target surface. The sensor may further comprise a speed measurement device that measures the speed at which the UVC-based aircraft sanitization system travels while irradiating the target surface, and the controller may be further configured to: receive speed feedback from the speed measurement device that measures the speed at which the UVC-based aircraft sanitization system travels while irradiating the target surface; generate a speed control command, based on the received speed feedback, that identifies a level of speed increase or speed decrease for the UVC-based aircraft sanitization system to achieve the desired radiation level at the target surface; and generate the UVC source control command for the UVC sources in the UVC-based aircraft sanitization system, based on the received measured radiation feedback and the speed feedback, to control the UVC sources to increase or decrease radiation level output to generate sufficient radiation to achieve the desired radiation level at the target surface. The sensor may further comprise a distance measurement device that measures the speed at which the UVC-based aircraft sanitization system travels while irradiating the target surface, and the controller may be further configured to: receive distance feedback from the distance measurement device that measures the distance between the UVC-based aircraft sanitization system and the target surface while the target surface may be irradiated; generate a distance control command, based on the received distance feedback, that identifies a level of distance increase or distance decrease for the UVC-based aircraft sanitization system to achieve the desired radiation level at the target surface; and generate the UVC source control command for the UVC sources in the UVC-based aircraft sanitization system, based on the received measured radiation feedback and the distance feedback, to control the UVC sources to increase or decrease radiation level output to generate sufficient radiation to achieve the desired radiation level at the target surface.

The sensor may further comprise a speed measurement device that measures the speed at which the UVC-based aircraft sanitization system travels while irradiating the target surface and a distance measurement device that measures the speed at which the UVC-based aircraft sanitization system travels while irradiating the target surface, and the controller may be further configured to: receive speed feedback from a speed measurement device that measures the speed at which the UVC-based aircraft sanitization system travels while irradiating the target surface; receive distance feedback from a distance measurement device that measures the distance between the UVC-based aircraft sanitization system and the target surface while the target surface may be irradiated; generate a distance control command, based on the received distance feedback, that identifies a level of distance increase or distance decrease for the UVC-based aircraft sanitization system to achieve the desired radiation level at the target surface; generate a speed control command, based on the received speed feedback, that identifies a level of speed increase or speed decrease for the UVC-based aircraft sanitization system to achieve the desired radiation level at the target surface; and generate the UVC source control command for the UVC sources in the UVC-based aircraft sanitization system, based on the received measured radiation feedback, the distance feedback, and the speed feedback, to control the UVC sources to increase or decrease radiation level output to generate sufficient radiation to achieve the desired radiation level at the target surface. The controller may be further configured to: receive environmental conditions feedback from one or more environmental sensors that measure environmental conditions including one or more of temperature and humidity; and generate the UVC source control command for the UVC sources in the UVC-based aircraft sanitization system, based on the received measured radiation feedback, the distance feedback, the speed feedback, and the environmental conditions feedback, to control the UVC sources to increase or decrease radiation level output to generate sufficient radiation to achieve the desired radiation level at the target surface. The controller may be further configured to: determine, based on the received radiation, distance, speed, and/or environmental conditions feedback, whether one or more of the UVC sources may be degraded; and provide an indication that indicates that one or more of the UVC sources are degraded when it may be determined that one or more of the UVC sources are degraded. The sensor feedback may comprise speed feedback and the sensor may comprise a speed measurement device that measures the speed at which the UVC-based aircraft sanitization system travels while irradiating the target surface, and wherein the controller may be configured to: generate a speed control command, based on the received speed feedback, that identifies a level of speed increase or speed decrease for the UVC-based aircraft sanitization system to achieve the desired radiation level at the target surface; and generate the UVC source control command for the UVC sources in the UVC-based aircraft sanitization system, based on the received speed feedback and the desired referenced speed at which the UVC sanitization system should travel, to control the UVC sources to increase or decrease radiation level output to generate sufficient radiation to achieve the desired radiation level at the target surface. The controller may be further configured to: receive distance feedback from a distance measurement device that measures the distance between the UVC-based aircraft sanitization system and the target surface while the target surface may be irradiated; generate a distance control command, based on the received distance feedback, that identifies a level of distance increase or distance decrease for the UVC-based aircraft sanitization system to achieve the desired radiation level at the target surface; and generate the UVC source control command for the UVC sources in the UVC-based aircraft sanitization system, based on the speed feedback and the distance feedback, to control the UVC sources to increase or decrease radiation level output to generate sufficient radiation to achieve the desired radiation level at the target surface. The controller may be further configured to: receive environmental conditions feedback from one or more environmental sensors that measure environmental conditions including one or more of temperature and humidity; and generate the UVC source control command for the UVC sources in the UVC-based aircraft sanitization system, based on the distance feedback, the speed feedback, and the environmental conditions feedback, to control the UVC sources to increase or decrease radiation level output to generate sufficient radiation to achieve the desired radiation level at the target surface. The sensor feedback may comprise distance feedback and the sensor may comprise a distance measurement device that measures the distance between the UVC-based aircraft sanitization system and the target surface while the target surface may be irradiated, and wherein the controller may be configured to: generate a distance control command, based on the received distance feedback, that identifies a level of distance increase or distance decrease for the UVC-based aircraft sanitization system to achieve the desired radiation level at the target surface; and generate the UVC source control command for the UVC sources in the UVC-based aircraft sanitization system, based on the received distance feedback, to control the UVC sources to increase or decrease radiation level output to generate sufficient radiation to achieve the desired radiation level at the target surface.

The control system may comprise: an outer feedback loop for receiving the measured radiation feedback from the radiation measurement device on the target surface and a referenced desired radiation level at the target surface and generating a dose error; and an inner feedback loop for receiving UVC source drive feedback and a UVC drive reference and generating the UVC source control command for the UVC sources, based on the dose error and the UVC source drive feedback, to control the UVC sources to increase or decrease radiation level output. The control system may further comprise a first intermediate feedback loop between the outer feedback loop and the inner feedback loop for receiving distance feedback and generating a distance error based on the dose error; and wherein the inner feedback loop may be configured to generate the UVC source control command for the UVC sources, based on the distance error and the UVC source drive feedback, to control the UVC sources to increase or decrease radiation level output. The control system may further comprise a second intermediate feedback loop between the outer feedback loop and the inner feedback loop for receiving speed feedback and generating a speed error based on the dose error; and wherein the inner feedback loop may be configured to generate the UVC source control command for the UVC sources, based on the speed error and the UVC source drive feedback, to control the UVC sources to increase or decrease radiation level output. The control system may further comprise: a first intermediate feedback loop between the outer feedback loop and the inner feedback loop for receiving distance feedback and generating a distance error based on the dose error; and a second intermediate feedback loop between the outer feedback loop and the inner feedback loop for receiving speed feedback and generating a speed error based on the dose error; wherein the inner feedback loop may be configured to generate the UVC source control command for the UVC sources, based on the distance error, the speed error and the UVC source drive feedback, to control the UVC sources to increase or decrease radiation level output. The dose error may be used to generate a UVC unit distance reference used in the first intermediate feedback loop to generate the distance error; the dose error may be used to generate a UVC speed unit reference used in the second intermediate feedback loop to generate the speed error; the distance error and the speed error may be used to generate a UVC drive reference used in the inner feedback loop to generate a drive error; and the drive error may be used to generate a UVC source drive reference for generating the UVC source control command for the UVC sources.

In another embodiment, a method for controlling a UVC-based aircraft sanitization system to maintain a desired UVC (ultraviolet C) radiation level at a target surface in an aircraft under varying operating conditions is provided. The method comprises: receiving sensor feedback from one or more sensors that measure a property from which a radiation level that is applied at the target surface by the UVC-based aircraft sanitization system can be determined, wherein the one or more sensors comprise a radiation measurement device that measures the radiation that is applied at the target surface, a speed measurement device that measures the speed at which the UVC-based aircraft sanitization system travels while irradiating the target surface, and/or a distance measurement device that measures the distance between the UVC-based aircraft sanitization system and the target surface while the target surface is irradiated; and generating a UVC source control command for UVC sources in the UVC-based aircraft sanitization system, based on the received sensor feedback, to control the UVC sources to increase or decrease radiation level output to generate sufficient radiation to achieve the desired radiation level at the target surface.

These aspects and other embodiments may include one or more of the following features. The receiving sensor feedback may comprise receiving one or more of measured radiation feedback that identifies a radiation level that is applied at the target surface by the UVC-based aircraft sanitization system, speed feedback from a speed measurement device that measures the speed at which the UVC-based aircraft sanitization system travels while irradiating the target surface, and/or distance feedback from a distance measurement device that measures the distance between the UVC-based aircraft sanitization system and the target surface while the target surface is irradiated, and the method may further comprise generating: a distance control command, based on the received distance feedback, that identifies a level of distance increase or distance decrease for the UVC-based aircraft sanitization system to achieve the desired radiation level at the target surface; a speed control command, based on the received speed feedback, that identifies a level of speed increase or speed decrease for the UVC-based aircraft sanitization system to achieve the desired radiation level at the target surface; and/or the UVC source control command for the UVC sources in the UVC-based aircraft sanitization system, based on the received measured radiation feedback, and/or the distance feedback, and/or the speed feedback and/or a referenced desired radiation level at the target surface, to control the UVC sources to increase or decrease radiation level output to generate sufficient radiation to achieve the desired radiation level at the target surface. The method may further comprise: receiving environmental conditions feedback from one or more environmental sensors that measure environmental conditions including one or more of temperature and humidity; and generating the UVC source control command for the UVC sources in the UVC-based aircraft sanitization system, based on the received measured radiation feedback, the distance feedback, the speed feedback, and the environmental conditions feedback, to control the UVC sources to increase or decrease radiation level output to generate sufficient radiation to achieve the desired radiation level at the target surface.

In another embodiment, non-transitory computer readable media encoded with programming instructions configurable to cause a processor in a control system of a UVC-based aircraft sanitization system to perform a method is provided. The method comprises: receiving sensor feedback from one or more sensors that measure a property from which a radiation level that is applied at the target surface by the UVC-based aircraft sanitization system can be determined, wherein the one or more sensors comprise a radiation measurement device that measures the radiation that is applied at the target surface, a speed measurement device that measures the speed at which the UVC-based aircraft sanitization system travels while irradiating the target surface, and/or a distance measurement device that measures the distance between the UVC-based aircraft sanitization system and the target surface while the target surface is irradiated; and generating a UVC source control command for UVC sources in the UVC-based aircraft sanitization system, based on the received sensor feedback, to control the UVC sources to increase or decrease radiation level output to generate sufficient radiation to achieve a desired radiation level at the target surface.

In another embodiment, a control system in a UVC-based aircraft sanitization system for controlling the UVC-based aircraft sanitization system to maintain a desired UVC (ultraviolet C) radiation level at a target surface in an aircraft under varying operating conditions is provided. The control system comprises a controller configured to: receive measured radiation feedback from a radiation measurement device (e.g., dosimeter) on the target surface that identifies a radiation level that is applied at the target surface by the UVC-based aircraft sanitization system; and generate a UVC source control command for UVC sources in the UVC-based aircraft sanitization system based on the received measured radiation feedback and a referenced desired radiation level at the target surface, to control the UVC sources to increase or decrease radiation level output (e.g., identify the amount of increase or decrease from the UVC sources) to generate sufficient radiation to achieve the desired radiation level at the target surface.

These aspects and other embodiments may include one or more of the following features. The controller may be further configured to: receive speed feedback from a speed measurement device that measures the speed at which the UVC-based aircraft sanitization system travels while irradiating the target surface; generate a speed control command, based on the received speed feedback, that identifies a level of speed increase or speed decrease for the UVC-based aircraft sanitization system to achieve the desired radiation level at the target surface; and generate the UVC source control command for UVC sources in the UVC-based aircraft sanitization system, based on the received measured radiation feedback and the speed feedback, to control the UVC sources to increase or decrease radiation level output to generate sufficient radiation to achieve the desired radiation level at the target surface. The controller may be further configured to: receive distance feedback from a distance measurement device that measures the distance between the UVC-based aircraft sanitization system and the target surface while the target surface may be irradiated; generate a distance control command, based on the received distance feedback, that identifies a level of distance increase or distance decrease for the UVC-based aircraft sanitization system to achieve the desired radiation level at the target surface; generate the UVC source control command for UVC sources in the UVC-based aircraft sanitization system, based on the received measured radiation feedback and the distance feedback, to control the UVC sources to increase or decrease radiation level output to generate sufficient radiation to achieve the desired radiation level at the target surface. The controller may be further configured to: receive speed feedback from a speed measurement device that measures the speed at which the UVC-based aircraft sanitization system travels while irradiating the target surface; receive distance feedback from a distance measurement device that measures the distance between the UVC-based aircraft sanitization system and the target surface while the target surface may be irradiated; generate a distance control command, based on the received distance feedback, that identifies a level of distance increase or distance decrease for the UVC-based aircraft sanitization system to achieve the desired radiation level at the target surface; generate a speed control command, based on the received speed feedback, that identifies a level of speed increase or speed decrease for the UVC-based aircraft sanitization system to achieve the desired radiation level at the target surface; and generate the UVC source control command for UVC sources in the UVC-based aircraft sanitization system, based on the received measured radiation feedback, the distance feedback, and the speed feedback, to control the UVC sources to increase or decrease radiation level output to generate sufficient radiation to achieve the desired radiation level at the target surface. The controller may be further configured to: receive environmental conditions feedback from one or more environmental sensors that measure environmental conditions including one or more of temperature and humidity; and generate the UVC source control command for UVC sources in the UVC-based aircraft sanitization system, based on the received measured radiation feedback, the distance feedback, the speed feedback, and the environmental conditions feedback, to control the UVC sources to increase or decrease radiation level output to generate sufficient radiation to achieve the desired radiation level at the target surface. The controller may be further configured to: determine, based on the received radiation, distance, speed, and/or environmental conditions feedback whether one or more of the UVC sources may be degraded; and provide an indication that indicates that one or more of the UVC sources are degraded when it may be determined that one or more of the UVC sources are degraded. The controller may be configured to determine whether one or more of the UVC sources may be degraded by comparing radiation levels measured at the target surface with an expected radiation level at the target surface determined based on the a level of output commanded via the UVC source control command and/or the level of speed commanded via the speed control command and/or the level of distance commanded via the distance control command. The controller may be further configured to generate a warning message indicating insufficient sanitization when the desired radiation level at the target surface may be not achievable through commands by the controller to adjust the radiation emitted by the UVC sources, adjust the speed of the UVC-based aircraft sanitization system up or down and/or adjust the path of the UVC-based aircraft sanitization system closer or further away from the target surface.

The control system may comprise: an outer feedback loop for receiving the measured radiation feedback from the radiation measurement device on the target surface and a referenced desired radiation level at the target surface and generating a dose error; and an inner feedback loop for receiving UVC source drive feedback and a UVC drive reference and generating the UVC source control command for the UVC sources, based on the dose error and the UVC source drive feedback, to control the UVC sources to increase or decrease radiation level output. The control system may further comprise a first intermediate feedback loop between the outer feedback loop and the inner feedback loop for receiving the distance feedback and generating a distance error based on the dose error; and wherein the inner feedback loop may be configured to generate the UVC source control command for the UVC sources, based on the distance error and the UVC source drive feedback, to control the UVC sources to increase or decrease radiation level output. The control system may further comprise a second intermediate feedback loop between the outer feedback loop and the inner feedback loop for receiving the speed feedback and generating a speed error based on the dose error; and wherein the inner feedback loop may be configured to generate the UVC source control command for the UVC sources, based on the speed error and the UVC source drive feedback, to control the UVC sources to increase or decrease radiation level output. The control system may further comprise: a first intermediate feedback loop between the outer feedback loop and the inner feedback loop for receiving the distance feedback and generating a distance error based on the dose error; and a second intermediate feedback loop between the outer feedback loop and the inner feedback loop for receiving the speed feedback and generating a speed error based on the dose error; wherein the inner feedback loop may be configured to generate the UVC source control command for the UVC sources, based on the distance error, the speed error and the UVC source drive feedback, to control the UVC sources to increase or decrease radiation level output. The dose error may be used to generate a UVC unit distance reference used in the first intermediate feedback loop to generate the distance error; the dose error may be used to generate a UVC speed unit reference used in the second intermediate feedback loop to generate the speed error; the distance error and the speed error may be used to generate a UVC drive reference used in the inner loop to generate a drive error; and the drive error may be used to generate a UVC source drive reference for generating the UVC source control command for the UVC sources.

In another embodiment, a method for controlling a UVC-based aircraft sanitization system to maintain a desired UVC (ultraviolet C) radiation level at a target surface in an aircraft under varying operating conditions is provided. The method comprises: receiving measured radiation feedback from a radiation measurement device (e.g., dosimeter) on the target surface that identifies a radiation level that is applied at the target surface by the UVC-based aircraft sanitization system; and generating a UVC source control command for UVC sources in the UVC-based aircraft sanitization system, based on the received measured radiation feedback, to control the UVC sources to increase or decrease radiation level output (e.g., identify the amount of increase or decrease from the UVC sources) to generate sufficient radiation to achieve the desired radiation level at the target surface.

These aspects and other embodiments may include one or more of the following features. The method may further comprise: receiving speed feedback from a speed measurement device that measures the speed at which the UVC-based aircraft sanitization system travels while irradiating the target surface; receiving distance feedback from a distance measurement device that measures the distance between the UVC-based aircraft sanitization system and the target surface while the target surface is irradiated; generating a distance control command, based on the received distance feedback, that identifies a level of distance increase or distance decrease for the UVC-based aircraft sanitization system to achieve the desired radiation level at the target surface; generating a speed control command, based on the received speed feedback, that identifies a level of speed increase or speed decrease for the UVC-based aircraft sanitization system to achieve the desired radiation level at the target surface; and generating the UVC source control command for UVC sources in the UVC-based aircraft sanitization system, based on the received measured radiation feedback, the distance feedback, and the speed feedback, to control the UVC sources to increase or decrease radiation level output to generate sufficient radiation to achieve the desired radiation level at the target surface. The method may further comprise: receiving environmental conditions feedback from one or more environmental sensors that measure environmental conditions including one or more of temperature and humidity; and generating the UVC source control command for UVC sources in the UVC-based aircraft sanitization system, based on the received measured radiation feedback, the distance feedback, the speed feedback, and the environmental conditions feedback, to control the UVC sources to increase or decrease radiation level output to generate sufficient radiation to achieve the desired radiation level at the target surface. The method may further comprise: determining, based on the received radiation, distance, speed, and/or environmental conditions feedback whether one or more of the UVC sources is degraded; and providing an indication that indicates that one or more of the UVC sources are degraded when it is determined that one or more of the UVC sources are degraded. The determining whether one or more of the UVC sources is degraded may comprise comparing radiation levels measured at the target surface with an expected radiation level at the target surface determined based on the a level of output commanded via the UVC source control command and/or the level of speed commanded via the speed control command and/or the level of distance commanded via the distance control command. The method may further comprise generating a warning message indicating insufficient sanitization when the desired radiation level at the target surface is not achievable through commands to adjust the radiation emitted by the UVC sources and/or adjust the speed of the UVC-based aircraft sanitization system up or down and/or adjust the path of the UVC-based aircraft sanitization system closer or further away from the target surface.

In another embodiment, non-transitory computer readable media encoded with programming instructions configurable to cause a processor in the control system of a UVC-based aircraft sanitization system to perform a method is provided. The method comprises: receiving measured radiation feedback from a radiation measurement device (e.g., dosimeter) on the target surface that identifies a radiation level that is applied at the target surface by the UVC-based aircraft sanitization system and a referenced desired radiation level at the target surface; and generating a UVC source control command for UVC sources in the UVC-based aircraft sanitization system, based on the received measured radiation feedback, to control the UVC sources to increase or decrease radiation level output (e.g., identify the amount of increase or decrease from the UVC sources) to generate sufficient radiation to achieve the desired radiation level at the target surface.

These aspects and other embodiments may include one or more of the following features. The method may further comprise: receiving speed feedback from a speed measurement device that measures the speed at which the UVC-based aircraft sanitization system travels while irradiating the target surface; receiving distance feedback from a distance measurement device that measures the distance between the UVC-based aircraft sanitization system and the target surface while the target surface is irradiated; generating a distance control command, based on the received distance feedback, that identifies a level of distance increase or distance decrease for the UVC-based aircraft sanitization system to achieve the desired radiation level at the target surface; generating a speed control command, based on the received speed feedback, that identifies a level of speed increase or speed decrease for the UVC-based aircraft sanitization system to achieve the desired radiation level at the target surface; and generating the UVC source control command for UVC sources in the UVC-based aircraft sanitization system, based on the received measured radiation feedback, the distance feedback, and the speed feedback, to control the UVC sources to increase or decrease radiation level output to generate sufficient radiation to achieve the desired radiation level at the target surface. The method may further comprise: receiving environmental conditions feedback from one or more environmental sensors that measure environmental conditions including one or more of temperature and humidity; and generating the UVC source control command for UVC sources in the UVC-based aircraft sanitization system, based on the received measured radiation feedback, the distance feedback, the speed feedback, and the environmental conditions feedback, to control the UVC sources to increase or decrease radiation level output to generate sufficient radiation to achieve the desired radiation level at the target surface. The method may further comprise: determining, based on the received radiation, distance, speed, and/or environmental conditions feedback whether one or more of the UVC sources is degraded; and providing an indication that indicates that one or more of the UVC sources are degraded when it is determined that one or more of the UVC sources are degraded. The determining whether one or more of the UVC sources is degraded may comprise comparing radiation levels measured at the target surface with an expected radiation level at the target surface determined based on the a level of output commanded via the UVC source control command and/or the level of speed commanded via the speed control command and/or the level of distance commanded via the distance control command. The method may further comprise generating a warning message indicating insufficient sanitization when the desired radiation level at the target surface is not achievable through commands to adjust the radiation emitted by the UVC sources and/or adjust the speed of the UVC-based aircraft sanitization system up or down and/or adjust the path of the UVC-based aircraft sanitization system closer or further away from the target surface.

In another embodiment, a control system in a UVC-based aircraft sanitization system for controlling the UVC-based aircraft sanitization system to maintain a desired UVC (ultraviolet C) radiation level at a target surface in an aircraft under varying operating conditions is provided. The control system includes a controller configured to: receive feedback from a plurality of sensors that provided an indication of a radiation level that is applied at the target surface. the sensors comprising one or more of a speedometer, dosimeter, and rangefinder; generate a control command for UVC sources in the UVC-based aircraft sanitization system, based on the feedback received, to control the UVC sources to generate sufficient radiation to achieve the desired radiation level at the target surface; provide a control command, based on the feedback received, for adjusting one or more of the speed of the UVC-based aircraft sanitization system up or down and/or the path of the UVC-based aircraft sanitization system closer or further away from the target surface when the UVC-based aircraft sanitization system is operating in a robotic mode to achieve the desired radiation level at the target surface; provide an indication, based on the feedback received, for an operator of the UVC-based aircraft sanitization system including one or more of indicating that the speed of the UVC-based aircraft sanitization system should be adjusted up or down, indicating that the path of the UVC-based aircraft sanitization system should be moved closer or further away from the target surface, and/or indicating that one or more of the UVC sources are degraded when the UVC-based aircraft sanitization system is operating in a manual mode; and generate a warning message indicating insufficient sanitization when the desired radiation level at the target surface is not achievable through commands by the controller to adjust the radiation emitted by the UVC sources, adjust the speed of the UVC-based aircraft sanitization system up or down and/or adjust the path of the UVC-based aircraft sanitization system closer or further away from the target surface.

These aspects and other embodiments may include one or more of the following features. The control system may comprise: an outer feedback loop for receiving UV dose feedback from the dosimeter and generating a dose error; an inner feedback loop for receiving UVC source drive feedback and generating a drive error; a first intermediate feedback loop between the outer feedback loop and the inner feedback loop for receiving UVC distance feedback and generating a distance error; and a second intermediate feedback loop between the outer feedback loop and the inner feedback loop for receiving UVC unit speed feedback and generating a speed error; wherein the dose error may be used to generate a UVC unit distance reference used in the first intermediate feedback loop to generate the distance error; wherein the dose error may be used to generate a UVC speed unit reference used in the second intermediate feedback loop to generate the speed error; wherein the distance error and the speed error are used to generate a UVC drive reference used in the inner loop to generate the drive error; and wherein the drive error may be used to generate a UVC source drive reference for generating the control command for the UVC sources. The controller may be further configured to receive environment sensor input from one or more of a temperature sensor and/or a humidity sensor; and wherein the environment sensor input may be used to generate the UVC source drive reference for generating the control command for the UVC sources.

In another embodiment, a control system in a UVC-based aircraft sanitization system for controlling the UVC-based aircraft sanitization system to maintain a desired UVC (ultraviolet C) radiation level at a target surface in an aircraft under varying operating conditions is provided. The control system comprises a controller configured to: receive distance feedback from a distance measurement device that measures the distance between the UVC-based aircraft sanitization system and the target surface while the target surface is irradiated; generate a distance control command, based on the received distance feedback, that identifies a level of distance increase or distance decrease for the UVC-based aircraft sanitization system to achieve the desired radiation level at the target surface; and generate a UVC source control command for the UVC sources in the UVC-based aircraft sanitization system, based on the distance feedback, to control the UVC sources to increase or decrease radiation level output to the target surface.

In another embodiment, a control system in a UVC-based aircraft sanitization system for controlling the UVC-based aircraft sanitization system to maintain a desired UVC (ultraviolet C) radiation level at a target surface in an aircraft under varying operating conditions is provided. The control system comprises a controller configured to: receive speed feedback from a speed measurement device that measures the speed at which the UVC-based aircraft sanitization system travels while irradiating the target surface; generate a speed control command, based on the received speed feedback, that identifies a level of speed increase or speed decrease for the UVC-based aircraft sanitization system to achieve the desired radiation level at the target surface; and generate a UVC source control command for UVC sources in the UVC-based aircraft sanitization system, based on the speed feedback, to control the UVC sources to increase or decrease radiation level output to the target surface.

Those of skill in the art will appreciate that the various illustrative logical blocks, modules, circuits, and algorithm steps described in connection with the embodiments disclosed herein may be implemented as electronic hardware, computer software, or combinations of both. Some of the embodiments and implementations are described above in terms of functional and/or logical block components (or modules) and various processing steps. However, it should be appreciated that such block components (or modules) may be realized by any number of hardware, software, and/or firmware components configured to perform the specified functions. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention. For example, an embodiment of a system or a component may employ various integrated circuit components, e.g., memory elements, digital signal processing elements, logic elements, look-up tables, or the like, which may carry out a variety of functions under the control of one or more microprocessors or other control devices. In addition, those skilled in the art will appreciate that embodiments described herein are merely exemplary implementations.

The various illustrative logical blocks, modules, and circuits described in connection with the embodiments disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

The steps of a method or algorithm described in connection with the embodiments disclosed herein may be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM, or any other form of storage medium known in the art. An exemplary storage medium is coupled to the processor such that the processor can read information from, and write information to, the storage medium. In the alternative, the storage medium may be integral to the processor. The processor and the storage medium may reside in an ASIC. The ASIC may reside in a user terminal. In the alternative, the processor and the storage medium may reside as discrete components in a user terminal.

In this document, relational terms such as first and second, and the like may be used solely to distinguish one entity or action from another entity or action without necessarily requiring or implying any actual such relationship or order between such entities or actions. Numerical ordinals such as "first," "second," "third," etc. simply denote different singles of a plurality and do not imply any order or sequence unless specifically defined by the claim language. The sequence of the text in any of the claims does not imply that process steps must be performed in a temporal or logical order according to such sequence unless it is specifically defined by the language of the claim. The process steps may be interchanged in any order without departing from the scope of the invention as long as such an interchange does not contradict the claim language and is not logically nonsensical.

Furthermore, depending on the context, words such as "connect" or "coupled to" used in describing a relationship between different elements do not imply that a direct physical connection must be made between these elements. For example, two elements may be connected to each other physically, electronically, logically, or in any other manner, through one or more additional elements.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

What is claimed is:

1. A control system in a UVC-based aircraft sanitization system for controlling the UVC-based aircraft sanitization system to maintain a desired UVC (ultraviolet C) radiation level at a target surface in an aircraft under varying operating conditions, the control system comprising:
 a sensor that measures a property from which a radiation level that is applied at the target surface by the UVC-based aircraft sanitization system can be determined, wherein the sensor comprises a radiation measurement device that measures the radiation level that is applied at the target surface;
 a controller configured to:
  receive sensor feedback from the sensor, wherein the sensor feedback comprises measured radiation feedback that identifies the radiation level that is applied at the target surface by the UVC-based aircraft sanitization system; and
  generate a UVC source control command for UVC sources in the UVC-based aircraft sanitization system, based on the received sensor feedback, to control the UVC sources to increase or decrease radiation level output to generate sufficient radiation to achieve the desired radiation level at the target surface;
 an outer feedback loop for receiving the measured radiation feedback from the radiation measurement device on the target surface and a referenced desired radiation level at the target surface and generating a dose error;
 an inner feedback loop for receiving UVC source drive feedback and a UVC drive reference and generating the UVC source control command for the UVC sources, based on the dose error and the UVC source drive feedback, to control the UVC sources to increase or decrease radiation level output;
 a first intermediate feedback loop between the outer feedback loop and the inner feedback loop for receiving distance feedback and generating a distance error based on the dose error; and
 a second intermediate feedback loop between the outer feedback loop and the inner feedback loop for receiving speed feedback and generating a speed error based on the dose error;
 wherein:
  the inner feedback loop is configured to generate the UVC source control command for the UVC sources, based on the distance error, the speed error and the UVC source drive feedback, to control the UVC sources to increase or decrease radiation level output; and
  the dose error is used to generate a UVC unit distance reference used in the first intermediate feedback loop to generate the distance error.

2. The control system of claim 1, wherein:
 the controller is configured to generate the UVC source control command for the UVC sources in the UVC-based aircraft sanitization system, based on the received measured radiation feedback and a referenced desired radiation level at the target surface, to control the UVC sources to increase or decrease radiation level output to generate sufficient radiation to achieve the desired radiation level at the target surface.

3. The control system of claim 2, wherein the sensor further comprises a speed measurement device that measures a speed at which the UVC-based aircraft sanitization system travels while irradiating the target surface, and the controller is further configured to:
 receive speed feedback from the speed measurement device that measures the speed at which the UVC-based aircraft sanitization system travels while irradiating the target surface;
 generate a speed control command, based on the received speed feedback, that identifies a level of speed increase or speed decrease for the UVC-based aircraft sanitization system to achieve the desired radiation level at the target surface; and
 generate the UVC source control command for the UVC sources in the UVC-based aircraft sanitization system, based on the received measured radiation feedback and the speed feedback, to control the UVC sources to increase or decrease radiation level output to generate sufficient radiation to achieve the desired radiation level at the target surface.

4. The control system of claim 2, wherein the sensor further comprises a distance measurement device that measures a distance between the UVC-based aircraft sanitization system and the target surface while the target surface is irradiated, and the controller is further configured to:
receive distance feedback from the distance measurement device that measures the distance between the UVC-based aircraft sanitization system and the target surface while the target surface is irradiated;
generate a distance control command, based on the distance feedback, that identifies a level of distance increase or distance decrease for the UVC-based aircraft sanitization system to achieve the desired radiation level at the target surface; and
generate the UVC source control command for the UVC sources in the UVC-based aircraft sanitization system, based on the received measured radiation feedback and the distance feedback, to control the UVC sources to increase or decrease radiation level output to generate sufficient radiation to achieve the desired radiation level at the target surface.

5. The control system of claim 2, wherein the sensor further comprises a speed measurement device that measures a speed at which the UVC-based aircraft sanitization system travels while irradiating the target surface and a distance measurement device that measures a distance between the UVC-based aircraft sanitization system and the target surface while the target surface is irradiated, and wherein the controller is further configured to:
receive speed feedback from the speed measurement device that measures the speed at which the UVC-based aircraft sanitization system travels while irradiating the target surface;
receive distance feedback from the distance measurement device that measures the distance between the UVC-based aircraft sanitization system and the target surface while the target surface is irradiated;
generate a distance control command, based on the distance feedback, that identifies a level of distance increase or distance decrease for the UVC-based aircraft sanitization system to achieve the desired radiation level at the target surface;
generate a speed control command, based on the received speed feedback, that identifies a level of speed increase or speed decrease for the UVC-based aircraft sanitization system to achieve the desired radiation level at the target surface; and
generate the UVC source control command for the UVC sources in the UVC-based aircraft sanitization system, based on the received measured radiation feedback, the distance feedback, and the speed feedback, to control the UVC sources to increase or decrease radiation level output to generate sufficient radiation to achieve the desired radiation level at the target surface.

6. The control system of claim 5, wherein the controller is further configured to:
receive environmental conditions feedback from one or more environmental sensors that measure environmental conditions including one or more of temperature and humidity; and
generate the UVC source control command for the UVC sources in the UVC-based aircraft sanitization system, based on the received measured radiation feedback, the distance feedback, the speed feedback, and the environmental conditions feedback, to control the UVC sources to increase or decrease radiation level output to generate sufficient radiation to achieve the desired radiation level at the target surface.

7. The control system of claim 6, wherein the controller is further configured to:
determine, based on one or more of the received radiation, distance, speed, or environmental conditions feedback, whether one or more of the UVC sources is degraded; and
provide an indication that indicates that one or more of the UVC sources are degraded when it is determined that one or more of the UVC sources are degraded.

8. The control system of claim 1, wherein the sensor feedback comprises speed feedback and the sensor comprises a speed measurement device that measures a speed at which the UVC-based aircraft sanitization system travels while irradiating the target surface, and wherein the controller is configured to:
generate a speed control command, based on the speed feedback, that identifies a level of speed increase or speed decrease for the UVC-based aircraft sanitization system to achieve the desired radiation level at the target surface; and
generate the UVC source control command for the UVC sources in the UVC-based aircraft sanitization system, based on the speed feedback and a desired referenced speed at which the UVC sanitization system should travel, to control the UVC sources to increase or decrease radiation level output to generate sufficient radiation to achieve the desired radiation level at the target surface.

9. The control system of claim 8, wherein the controller is further configured to:
receive distance feedback from a distance measurement device that measures a distance between the UVC-based aircraft sanitization system and the target surface while the target surface is irradiated;
generate a distance control command, based on the distance feedback, that identifies a level of distance increase or distance decrease for the UVC-based aircraft sanitization system to achieve the desired radiation level at the target surface; and
generate the UVC source control command for the UVC sources in the UVC-based aircraft sanitization system, based on the speed feedback and the distance feedback, to control the UVC sources to increase or decrease radiation level output to generate sufficient radiation to achieve the desired radiation level at the target surface.

10. The control system of claim 9, wherein the controller is further configured to:
receive environmental conditions feedback from one or more environmental sensors that measure environmental conditions including one or more of temperature and humidity; and
generate the UVC source control command for the UVC sources in the UVC-based aircraft sanitization system, based on the distance feedback, the speed feedback, and the environmental conditions feedback, to control the UVC sources to increase or decrease radiation level output to generate sufficient radiation to achieve the desired radiation level at the target surface.

11. The control system of claim 1, wherein the sensor feedback comprises distance feedback and the sensor comprises a distance measurement device that measures a distance between the UVC-based aircraft sanitization system and the target surface while the target surface is irradiated, and wherein the controller is configured to:
- generate a distance control command, based on the distance feedback, that identifies a level of distance increase or distance decrease for the UVC-based aircraft sanitization system to achieve the desired radiation level at the target surface; and
- generate the UVC source control command for the UVC sources in the UVC-based aircraft sanitization system, based on the distance feedback, to control the UVC sources to increase or decrease radiation level output to generate sufficient radiation to achieve the desired radiation level at the target surface.

12. The control system of claim 1, wherein the dose error is used to generate a UVC speed unit reference used in the second intermediate feedback loop to generate the speed error.

13. The control system of claim 12, wherein the distance error and the speed error are used to generate a UVC drive reference used in the inner feedback loop to generate a drive error.

14. The control system of claim 13, wherein the drive error is used to generate a UVC source drive reference for generating the UVC source control command for the UVC sources.

15. A UVC-based aircraft sanitization system, comprising:
- a plurality of UVC sources;
- a sensor that measures a property from which a radiation level that is applied at a target surface in an aircraft by the UVC-based aircraft sanitization system can be determined, wherein the sensor comprises one or more of a radiation measurement device that measures a radiation level that is applied at the target surface, a speed measurement device that measures a speed at which the UVC-based aircraft sanitization system travels while irradiating the target surface, or a distance measurement device that measures a distance between the UVC-based aircraft sanitization system and the target surface while the target surface is irradiated;
- a controller configured to:
  - receive sensor feedback from the sensor, wherein the sensor feedback comprises measured radiation feedback that identifies a radiation level that is applied at the target surface by the UVC-based aircraft sanitization system; and
  - generate a UVC source control command for the plurality of UVC sources, based on the sensor feedback, to control the UVC sources to increase or decrease radiation level output to generate sufficient radiation to achieve a desired radiation level at the target surface in the aircraft;
- an outer feedback loop for receiving the measured radiation feedback from the radiation measurement device on the target surface and a referenced desired radiation level at the target surface and generating a dose error;
- an inner feedback loop for receiving UVC source drive feedback and a UVC drive reference and generating the UVC source control command for the UVC sources, based on the dose error and the UVC source drive feedback, to control the UVC sources to increase or decrease radiation level output;
- a first intermediate feedback loop between the outer feedback loop and the inner feedback loop for receiving distance feedback and generating a distance error based on the dose error; and
- a second intermediate feedback loop between the outer feedback loop and the inner feedback loop for receiving speed feedback and generating a speed error based on the dose error;

wherein:
- the inner feedback loop is configured to generate the UVC source control command for the UVC sources, based on the distance error, the speed error and the UVC source drive feedback, to control the UVC sources to increase or decrease radiation level output;
- the dose error is used to generate a UVC unit distance reference used in the first intermediate feedback loop to generate the distance error; and
- the dose error is used to generate a UVC speed unit reference used in the second intermediate feedback loop to generate the speed error.

16. The UVC-based aircraft sanitization system of claim 15, wherein the sensor feedback comprises one or more of measured radiation feedback that identifies a radiation level that is applied at the target surface by the UVC-based aircraft sanitization system, speed feedback from a speed measurement device that measures the speed at which the UVC-based aircraft sanitization system travels while irradiating the target surface, or distance feedback from a distance measurement device that measures the distance between the UVC-based aircraft sanitization system and the target surface while the target surface is irradiated, and wherein the controller is further configured to generate one or more of:
- a distance control command, based on the distance feedback, that identifies a level of distance increase or distance decrease for the UVC-based aircraft sanitization system to achieve the desired radiation level at the target surface;
- a speed control command, based on the received speed feedback, that identifies a level of speed increase or speed decrease for the UVC-based aircraft sanitization system to achieve the desired radiation level at the target surface; or
- the UVC source control command for the UVC sources in the UVC-based aircraft sanitization system, based on one or more of the received measured radiation feedback, the distance feedback, the speed feedback or a referenced desired radiation level at the target surface, to control the UVC sources to increase or decrease radiation level output to generate sufficient radiation to achieve the desired radiation level at the target surface.

17. The UVC-based aircraft sanitization system of claim 16, wherein the controller is further configured to:
- receive environmental conditions feedback from one or more environmental sensors that measure environmental conditions including one or more of temperature and humidity; and
- generate the UVC source control command for the UVC sources in the UVC-based aircraft sanitization system, based on the received measured radiation feedback, the distance feedback, the speed feedback, and the environmental conditions feedback, to control the UVC sources to increase or decrease radiation level output to generate sufficient radiation to achieve the desired radiation level at the target surface.

18. The UVC-based aircraft sanitization system of claim 17, wherein the controller is further configured to:
- determine, based on one or more of the received radiation, distance, speed, or environmental conditions feedback, whether one or more of the UVC sources is degraded; and provide an indication that indicates that one or more of the UVC sources are degraded when it is determined that one or more of the UVC sources are degraded.

19. The UVC-based aircraft sanitization system of claim 18, wherein the distance error and the speed error are used to generate a UVC drive reference used in the inner feedback loop to generate a drive error.

20. The UVC-based aircraft sanitization system of claim 19, wherein the drive error is used to generate a UVC source drive reference for generating the UVC source control command for the UVC sources.

\* \* \* \* \*